United States Patent
Melman

(10) Patent No.: US 9,592,014 B2
(45) Date of Patent: Mar. 14, 2017

(54) X-RAY REDUCTION SYSTEM

(71) Applicant: CONTROLRAD SYSTEMS, INC., Radnor, PA (US)

(72) Inventor: Haim Zvi Melman, Kfar Saba (IL)

(73) Assignee: CONTROLRAD SYSTEMS INC., Radnor, PA (US)

( * ) Notice: Subject to any disclaimer, the term of this patent is extended or adjusted under 35 U.S.C. 154(b) by 204 days.

(21) Appl. No.: 14/380,743

(22) PCT Filed: Feb. 26, 2013

(86) PCT No.: PCT/IB2013/051541
§ 371 (c)(1),
(2) Date: Aug. 25, 2014

(87) PCT Pub. No.: WO2013/132387
PCT Pub. Date: Sep. 12, 2013

(65) Prior Publication Data
US 2015/0023466 A1    Jan. 22, 2015

Related U.S. Application Data

(60) Provisional application No. 61/606,375, filed on Mar. 3, 2012.

(51) Int. Cl.
*A61B 6/06* (2006.01)
*A61B 6/08* (2006.01)
*A61B 6/00* (2006.01)

(52) U.S. Cl.
CPC ............ *A61B 6/06* (2013.01); *A61B 6/08* (2013.01); *A61B 6/469* (2013.01); *A61B 6/485* (2013.01); *A61B 6/487* (2013.01); *A61B 6/52* (2013.01); *A61B 6/5205* (2013.01); *A61B 6/542* (2013.01); *A61B 6/545* (2013.01); *A61B 6/582* (2013.01)

(58) Field of Classification Search
CPC ........................................................ A61B 6/06
See application file for complete search history.

(56) References Cited

U.S. PATENT DOCUMENTS 3,717,768 A * 2/1973 Edholm ................ A61B 6/032
378/156
5,091,926 A  2/1992 Horton et al.
(Continued)

FOREIGN PATENT DOCUMENTS

FR        2155168 A5    5/1973
JP     H08280657 A    10/1996
(Continued)

*Primary Examiner* — Charlie Y Peng

(57) ABSTRACT

An x-ray system comprising an x-ray source, a single essentially round collimator, a camera, a detector and a monitor, means for moving the collimator in a plane generally parallel to the plane of the collimator; and the collimator comprising a central aperture that allows all the radiation to pass through, an outer annulus that reduces the radiation passing through at an amount depending on the material and the thickness of the material and an inner annulus between the central aperture and the outer annulus, with thickness changing as a function of the distance from the center, starting at thickness zero on the side of the central aperture and ending at the thickness of the outer annulus on the side of the outer annulus.

2 Claims, 18 Drawing Sheets

(56) References Cited

U.S. PATENT DOCUMENTS

| | | | | |
|---|---|---|---|---|
| 5,095,906 | A | * | 3/1992 | Ema .......................... G06T 5/50 378/98.12 |
| 5,282,254 | A | | 1/1994 | Chiu et al. |
| 5,369,678 | A | * | 11/1994 | Chiu ........................ A61B 6/12 378/152 |
| 5,568,533 | A | * | 10/1996 | Kumazaki ................ G21K 1/04 378/156 |
| 6,731,783 | B2 | * | 5/2004 | Tsujii ....................... H05G 1/60 250/582 |
| 2008/0037708 | A1 | * | 2/2008 | Kuzmanovic ............ A61B 6/08 378/62 |
| 2008/0118023 | A1 | | 5/2008 | Besson |
| 2008/0253519 | A1 | * | 10/2008 | Bonfiglio ................. A61B 6/00 378/65 |
| 2012/0187312 | A1 | * | 7/2012 | Guez ........................ A44C 5/20 250/492.1 |

FOREIGN PATENT DOCUMENTS

| | | |
|---|---|---|
| JP | 2005118382 A | 5/2005 |
| WO | 2012125978 A1 | 9/2012 |

\* cited by examiner

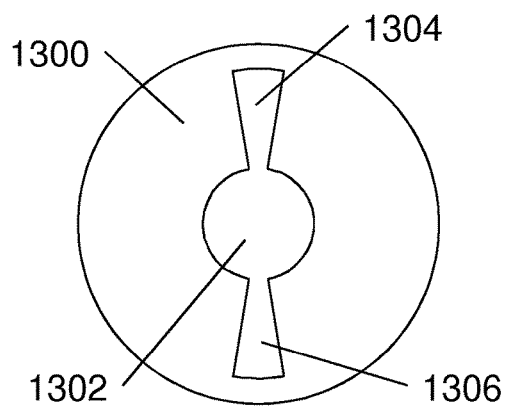
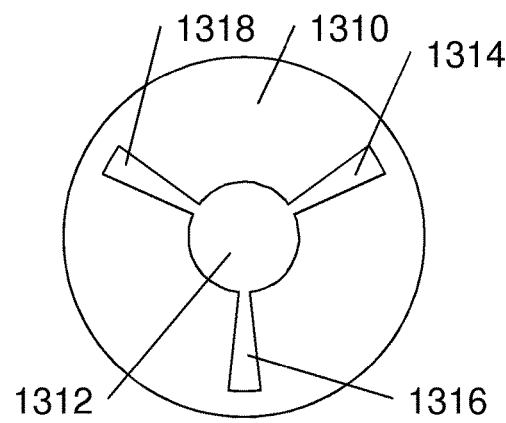
Figure 13A  Figure 13B
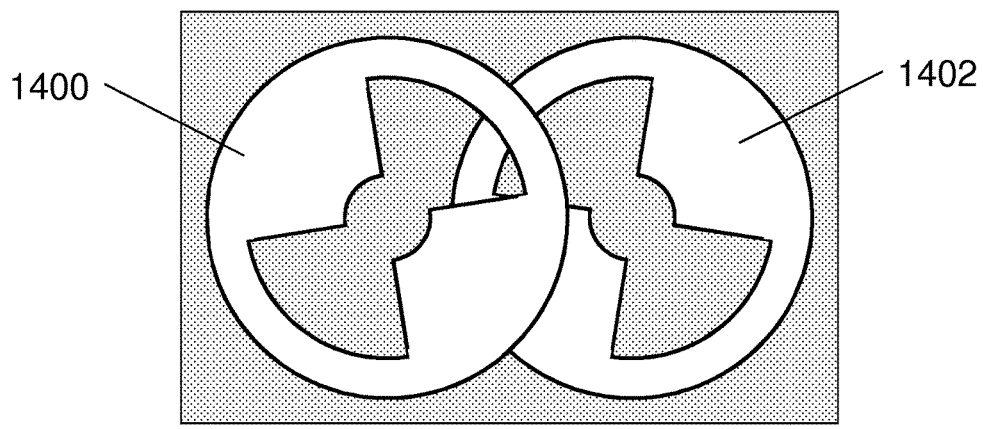
Figure 14A
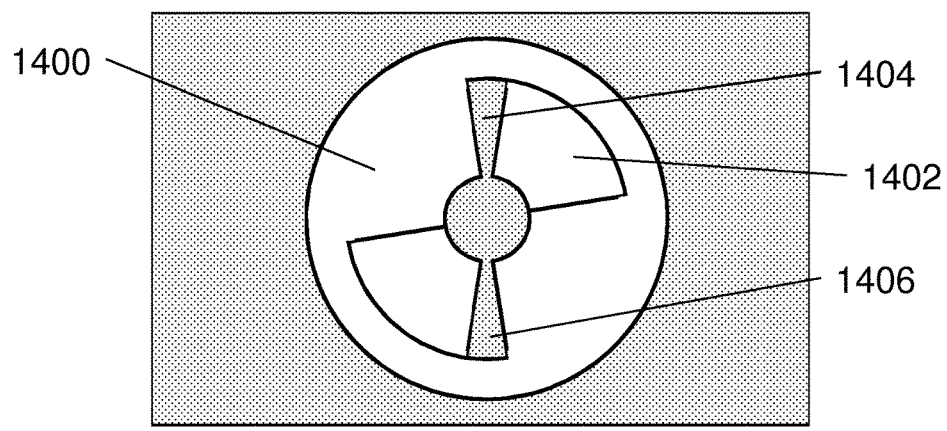
Figure 14B

X-RAY REDUCTION SYSTEM

CROSS-REFERENCE TO RELATED PATENT APPLICATIONS

This patent application claims priority from and is related to U.S. Provisional Patent Application Ser. No. 61/606,375, filed Mar. 3, 2012, this U.S. Provisional Patent Application incorporated by reference in its entirety herein.

FIELD OF THE INVENTION

The invention is related to the field of fluoroscopy and more particularly to the field of controlling x-ray radiation amount during fluoroscopy.

BACKGROUND OF THE INVENTION

In a typical fluoroscopy system the x-ray tube generates x-ray radiation over a relatively wide solid angle. To avoid unnecessary exposure to both the patient and the medical team, collimators of x-ray absorbing materials such as lead are used to block the redundant radiation. This way only the necessary solid angle of useful radiation exits the x-ray tube to expose only the necessary elements.

Such collimators are used typically in a static mode but may assume a variety of designs and x-ray radiation geometry. Collimators can be set up manually or automatically using as input, for example, the dimensions of the organ environment that is involved in the procedure.

In fluoroscopy the situation is more dynamic than in a single exposure x-ray. The x-ray radiation is active for relatively long period and the treating physician typically has to stand near the patient, therefore near the x-ray radiation. As a result, it is desired to provide methods to minimize exposure to the medical team. Methods for reducing x-ray radiation intensity have been suggested where the resultant reduced signal to noise ratio (S/N) of the x-ray image in compensated by digital image enhancement. Other methods suggest a collimator limiting the solid angle of the x-ray radiation to a fraction of the image intensifier area and moving the collimator to swap the entire input area of the image intensifier where the Region of Interest (ROI) is exposed more than the rest of the area. This way, the ROI gets high enough x-ray radiation to generate a good S/N image while the rest of the image is exposed with low x-ray intensity, providing a relatively low S/N image. The ROI size and position can be determined in a plurality of methods. For example, it can be a fixed area in the center of the image or it can be centered automatically about the most active area in the image, this activity is determined by temporal image analysis of s sequence of cine images received from the video camera of the fluoroscopic system.

A SUMMARY OF THE INVENTION

According to a first aspect of the present invention there is provided an x-ray system comprising an x-ray source, a single essentially round collimator, a detector, a monitor and means for rotating said collimator about an axis generally perpendicular to the plane of said collimator; wherein said collimator is constructed from a region essentially opaque to x-ray radiation and a region that is transparent to x-ray.

The detector may comprise means for integrating signals during 360 degrees rotation (exposure cycle) of said collimator, said system additionally comprising means for reading frames comprising pixel values from said detector.

The means for reading may comprise means for reading pixel values at the end of each exposure cycle.

The means for reading may comprise means for reading pixel values at the end of an integer number of exposure cycles.

The means for reading may comprise means for reading pixel values before the end of an exposure cycle.

The number of frames read during an exposure cycle may be an integer.

The system may additionally comprise means for calculating gain and offset correction for each frame and means for calculating normalization factors for each frame, according to the collimator shape, speed and position.

The system may additionally be configured to generate an exposure image by correcting and summing all the frames read within an exposure cycle.

The system may additionally be configured to generate an exposure image by correcting and summing the last read N frames after each reading of a frame.

The system may additionally be configured to generate an exposure image by correcting and summing all the exposed pixels in the frames read within an exposure cycle.

The system may additionally be configured to generate an exposure image by correcting and summing all the exposed pixels in the last read N frames after each reading of a frame.

The means for calculating normalization factors for each frame may comprise means for multiplying pixels values by theoretical factors that compensate for the difference in DPP.

The means for calculating normalization factors for each frame may comprise means for acquiring calibration frames and means for calculating calibration factors for each pixel based on said calibration frames.

The calibration frames may comprise averages of a plurality of frames.

The calibration frames may comprise one frame captured with x-ray radiation on and one frame captured with x-ray radiation off.

The means for calculating normalization factors for each frame may comprise means for calculating bi-linear corrections.

The system may additionally comprise means for generating an exposure image from said corrected frame and means for refreshing said exposure image.

The means for refreshing may comprise means for using different refreshment rates for different areas of said image.

The means for reading may comprise means for sequentially accessing and reading an entire frame from said detector.

The transparent region may be the combination of a circular hole concentric with the center of rotation of said collimator and a hole in the shape of a sector of a circle concentric with the center of rotation of said collimator and spanning an angle.

The collimator may additionally comprise a balancing weight.

The frame may comprise pixels associated with said circular hole having received a first dose of x-ray radiation and pixels associated with collimator regions surrounding said circular hole having received a second dose of x-ray radiation, said second dose comprising a fraction of said first dose, said fraction proportional to the ratio of sector angle to 360 degrees.

The means for reading may comprise means for randomly accessing and reading pixels from said detector.

The means for reading may be configured to read pixel values from a first fully exposed sector adjacent a currently exposed sector and reset said pixels after reading.

The angular span of said first sector may be selected such that the time required for reading and resetting the pixels in said first sector does not exceed the time required for said collimator to rotate the same angular distance.

The system may be additionally configured to reset pixel values in a second sector about to be exposed, said second sector adjacent a currently exposed sector.

The collimator may additionally comprise synchronization means for synchronizing the detector with the collimator rotation.

The synchronization means may comprise a tab constructed on the collimator that passes through a photosensor.

The synchronization means may comprise an encoder.

The means for rotating the collimator may comprise a first pulley mounted on top of the collimator in a concentric location to the collimator; a second pulley mounted on a motor; a belt connecting the first pulley with the second pulley; a V-shape circular track concentric with collimator; and three wheels in contact with the V-groove of said track, the rotation axes of the three wheels mounted on an annulus shaped static part that is fixed to the reference frame of the x-ray tube.

The belt may be selected from the group consisting of: a flat belt, a round belt, a V-belt, a multi-groove belt, a ribbed belt, a film belt and a timing belt.

The means for rotating the collimator may comprise gear transmission.

The gear transmission may be selected from the group consisting of: spur, helical, bevel, hypoid, crown and worm gears.

The means for rotating the collimator may comprise a high friction rotating surface cylinder in direct contact with the rim of the collimator.

The collimator may comprise a fixed aperture.

The collimator may comprise a variable aperture.

The system may comprise means for mounting two concentric fixed-aperture collimator and means for rotating said two collimator one relative to the other.

The system may comprise means for rotating each one of said two collimators independently.

The system may comprise means for rotating each one of said two collimators in a different speed.

The system may comprise means for rotating said collimator at variable speed.

The collimator may comprise an aperture shape designed to provide, at a constant rotation speed, two areas with two different radiation doses per pixel (DPP).

The collimator may comprise a qualitative exposure profile providing different levels of DPP for different distances from the collimator center.

The system may additionally comprise an eye tracker, the system configured to track an operator's gaze, determine thereby a region of interest (ROI) and control said collimator accordingly.

According to a second aspect of the present invention there is provided an x-ray system comprising an x-ray source, a single essentially round collimator, a camera, a detector and a monitor, means for moving said collimator in a plane generally parallel to the plane of said collimator; and said collimator comprising a central aperture that allows all the radiation to pass through, an outer annulus that reduces the radiation passing through at an amount depending on the material and the thickness of the material and an inner annulus between said central aperture and said outer annulus, with thickness changing as a function of the distance from the center, starting at thickness zero on the side of the central aperture and ending at the thickness of the outer annulus on the side of the outer annulus.

The detector may be configured to integrate signals of each frame captured by said camera, said system additionally configured to read frames comprising pixels from said detector.

The system may be configured to read a frame at the end of each frame capture by the camera.

The system may be additionally configured to calculate gain and offset correction for each frame and to calculate normalization factors for each frame, according to the different DPP in each of said aperture, said outer annulus and said inner annulus of the collimator.

The system may be additionally configured to calculate said normalization factors for said inner annulus by dividing said inner annulus into a plurality of annuli and assigning a theoretical DPP to each said plurality of annuli depending on its distance from said central aperture.

The system may additionally comprise an eye tracker, the system configured to track an operator's gaze, determine thereby a region of interest (ROI) and control said collimator accordingly.

According to a third aspect of the present invention there is provided a method of enhancing a displayed exposure image in a x-ray system comprising a x-ray source, a single essentially round collimator, a detector, a monitor and means for rotating said collimator about an axis generally perpendicular to the plane of said collimator, said collimator constructed from a region essentially opaque to x-ray radiation and a region that is transparent to x-ray, comprising: capturing by said detector an image from said x-ray source; integrating signals by said detector during 360 degrees rotation (exposure cycle) of said collimator; reading frames comprising pixel values from said detector; calculating gain and offset correction for each frame; calculating normalization factors for each frame, according to the collimator shape, speed and position; generating an exposure image from said corrected frame; and refreshing said exposure image.

The reading may comprise reading pixel values at the end of each exposure cycle.

The reading may comprise reading pixel values at the end of an integer number of exposure cycles.

The reading may comprise reading pixel values before the end of an exposure cycle.

The number of frames read during an exposure cycle may be an integer.

The generating an exposure image may comprise correcting and summing all the frames read within an exposure cycle.

The generating an exposure image may comprise correcting and summing the last read N frames after each reading of a frame.

The generating an exposure image may comprise correcting and summing all the exposed pixels in the frames read within an exposure cycle.

The generating an exposure image may comprise correcting and summing all the exposed pixels in the last read N frames after each reading of a frame.

The calculating normalization factors for each frame may comprise multiplying pixels values by theoretical factors that compensate for the difference in DPP.

The calculating normalization factors for each frame may comprise acquiring calibration frames and calculating calibration factors for each pixel based on said calibration frames.

The calibration frames may comprise averages of a plurality of frames.

The calibration frames may comprise one frame captured with x-ray radiation on and one frame captured with x-ray radiation off.

The calculating normalization factors for each frame may comprise calculating bi-linear corrections.

The refreshing may comprise using different refreshment rates for different areas of said image.

The reading may comprise sequentially accessing and reading an entire frame from said detector.

The transparent region may be the combination of a circular hole concentric with the center of rotation of said collimator and a hole in the shape of a sector of a circle concentric with the center of rotation of said collimator and spanning an angle, wherein said frame comprise pixels associated with said circular hole having received a first dose of x-ray radiation and pixels associated with collimator regions surrounding said circular hole having received a second dose of x-ray radiation, said second dose comprising a fraction of said first dose, said fraction proportional to the ratio of sector angle to 360 degrees, wherein said reading comprises randomly accessing and reading pixels from said detector.

The reading may comprise reading pixel values from a first fully exposed sector adjacent a currently exposed sector and resetting said pixels after reading.

The angular span of said first sector may be selected such that the time required for reading and resetting the pixels in said first sector does not exceed the time required for said collimator to rotate the same angular distance.

The method may additionally comprise resetting pixel values in a second sector about to be exposed, said second sector adjacent a currently exposed sector.

The method may further comprise tracking an operator's gaze, determining thereby a region of interest (ROI) and controlling said collimator accordingly.

According to a fourth aspect of the present invention there is provided a method of enhancing a displayed exposure image in a x-ray system comprising a x-ray source, a single essentially round collimator, a camera, a detector and a monitor, means for moving said collimator in a plane generally parallel to the plane of said collimator, said collimator comprising a central aperture that allows all the radiation to pass through, an outer annulus that reduces the radiation passing through at an amount depending on the material and the thickness of the material and an inner annulus between said central aperture and said outer annulus, with thickness changing as a function of the distance from the center, starting at thickness zero on the side of the central aperture and ending at the thickness of the outer annulus on the side of the outer annulus, comprising: integrating by said detector signals of each frame captured by said camera; reading frames comprising pixels from said detector; calculating gain and offset correction for each frame; and calculating normalization factors for each frame, according to the different DPP in each of said central aperture, said outer annulus and said inner annulus of the collimator.

The reading may comprise reading a frame at the end of each frame capture by the camera.

The calculating normalization factors for said inner annulus may comprise dividing said inner annulus into a plurality of annuli and assigning a theoretical DPP to each said plurality of annuli depending on its distance from said central aperture.

The method may further comprise tracking an operator's gaze, determining thereby a region of interest (ROI) and controlling said collimator accordingly.

BRIEF DESCRIPTION OF THE DRAWINGS

For a better understanding of the invention and to show how the same may be carried into effect, reference will now be made, purely by way of example, to the accompanying drawings.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings:

FIG. 13A is a schematic illustration of another example of a collimator of the invention;

FIG. 13B is a schematic illustration of another example of a collimator of the invention;

FIG. 14A is a schematic illustration of the main parts of another example of a collimator of the invention;

FIG. 14B is a schematic illustration of the parts of FIG. 14A in the operative configuration;

A DETAILED DESCRIPTION OF THE INVENTION

Figure 1A:
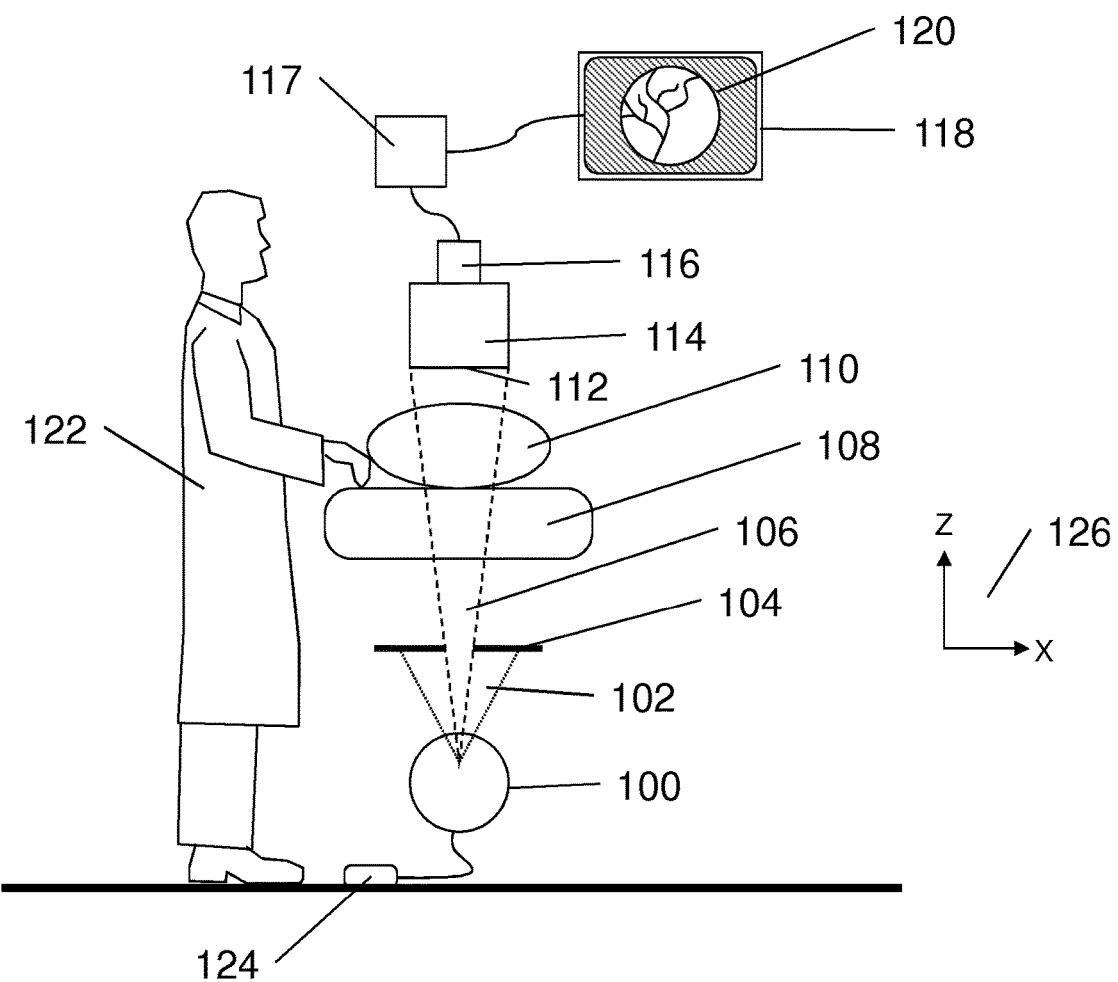
FIG. 1A is a simplified schematic illustration of an example layout of a fluoroscopy clinical environment and system.

Reference is made now to FIG. 1A which presents a typical layout of a fluoroscopy clinical environment.

X-ray tube 100 generates x-ray radiation 102 directed upward occupying a relatively large solid angle towards collimator 104. Collimator 104 blocks a part of the radiation allowing a smaller solid angle of radiation to continue in the upward direction, go through bed 108 that is typically made of material that is relatively transparent to x-ray radiation and through patient 110 who is laying on bed 108. part of the radiation is absorbed and scattered by the patient and the remaining radiation arrives at the typically round input area 112 of image intensifier 114. The input area of the image intensifier is typically in the order of 300 mm in diameter but may vary per the model and the technology. The image generated by image intensifier 114 is captured by camera, 116 processed by image processor 117 and then displayed on monitor 118 as image 120.

Although the invention is described mainly in reference to the combination of image intensifier 114 and camera 116 it would be appreciated that both these elements can be replaced by a digital radiography sensor of any technology such as CCD or CMOS flat panels or other technologies such as Amorphous Silicon with scintillatiors located at plane 112. One such example is CXDI-50RF Available from Canon U.S.A., Inc., Lake Success, N.Y. The term "detector" will be used to include any of these technologies, including the combination of any image intensifier with any camera and including any type of a flat panel sensor or any other device converting x-ray to electronic signal. The terms "area" and "region" are used alternatively in the detailed description of the invention any they mean the same and are used as synonyms.

The term "x-ray source" will be used to provide a wide interpretation for a device having x-ray point source that does not necessarily have the shape of a tube. Although the term x-ray tube is used in the examples of the invention in convention with common terminology in the art, it is represented here that the examples of the invention are not limited to a narrow interpretation of x-ray tube and that any x-ray source can be used in these examples (for example even radioactive material configured to function as a point source).

Operator 122 is standing by the patient to perform the medical procedure while watching image 120.

The operator has a foot-switch 124. When pressing the switch, continuous x-ray radiation (or relatively high frequency pulsed x-ray as explained below) is emitted to provide a cine imaging 120. The intensity of x-ray radiation is typically optimized in a tradeoff of low intensity that is desired to reduce exposure to the patient and the operator and high intensity radiation that is desired to enable a high quality image 120 (high S/N). With low intensity x-ray radiation and thus low exposure of the image intensifier input area, the S/N of image 120 might be so low that image 120 becomes useless.

Coordinate system 126 is a reference Cartesian coordinate system with Y axis pointing into the page and X-Y is a plane parallel to planes such as that of collimator 104 and image intensifier input plane 112.

It is a purpose of the present invention to provide high exposure at the input area of the image intensifier in the desired ROI that will provide therefore a high S/N image there while reducing the exposure of other sections of the image intensifier area, at the cost of lower image quality (lower S/N). With this arrangement the operator can see a clear image in the ROI and get a good enough image for general orientation in the rest of the image area. It is also the purpose of this invention to provide more complex map of segments in the image where each segment results from a different level of x-ray radiation as desired by the specific application. It is also the purpose of the current invention to provide various methods to read the data off the image sensor.

In the context of the examples provided throughout the detailed description of the invention, when S/N of one area is compared to S/N in another area the S/N are compared for pixels that have the same object (such as patient and operators hands and tools) transmittance. For example, when an area A is described has as having lower S/N than area B it is assumed that the transmission of x-ray by the object to both areas is uniform over the area and is the same. For example, at the center of the area A only ½ of the radiation arriving at the object is transmitted through to the image intensifier then, S/N in area B is compared to area A for an area B that also only ½ of the radiation arriving at the object is transmitted through to the image intensifier.

The S (signal) of area A is the average reading value of the area A (average over time or over the area if it includes enough pixels in the statistical sense. The S (signal) of area B is the average reading value of the area B (average over time or over the area if it includes enough pixels in the statistical sense. To simplify discussion scattered radiation is not considered in the detailed description of the invention. The affect of scattered radiation and means to reduce it are well known in the art.

In the examples below the noise statistics is assumed to be of Gaussian distribution which satisfies most practical aspects of implementation of the invention and serves well clear presentations of examples of the detailed description of the invention. This is not a limitation of the invention and, if desired, the mathematics presented in association to Gaussian statistics can be replaced by that of Poisson statistics (or other statistics) without degrading the scope of the invention. The noise values associated with each signal are represented by the standard deviation of the Poisson statistics for that signal, known in the art as Poisson Noise.

Also dose per pixel (DPP) throughout the detailed description of the invention is discussed in the same sense, i.e. the when the DPP of pixel A is compared to DPP of pixel B it is assumed the object transmission for both pixels is the same.

Figure 1B:
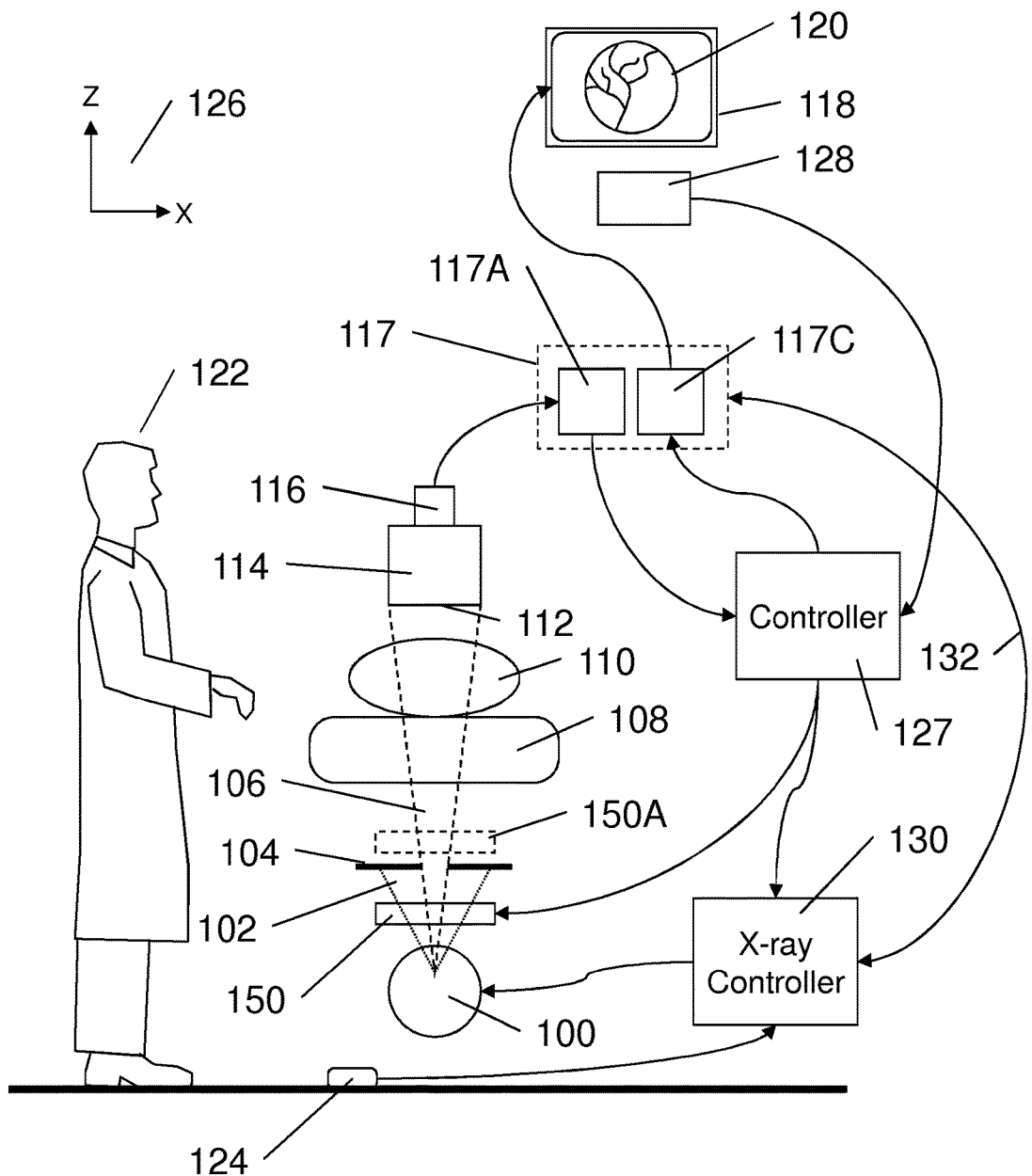
FIG. 1B is an illustration of an example of a layout of the system of FIG. 1A showing additional details of components of the system example of the invention.
Figure 21:
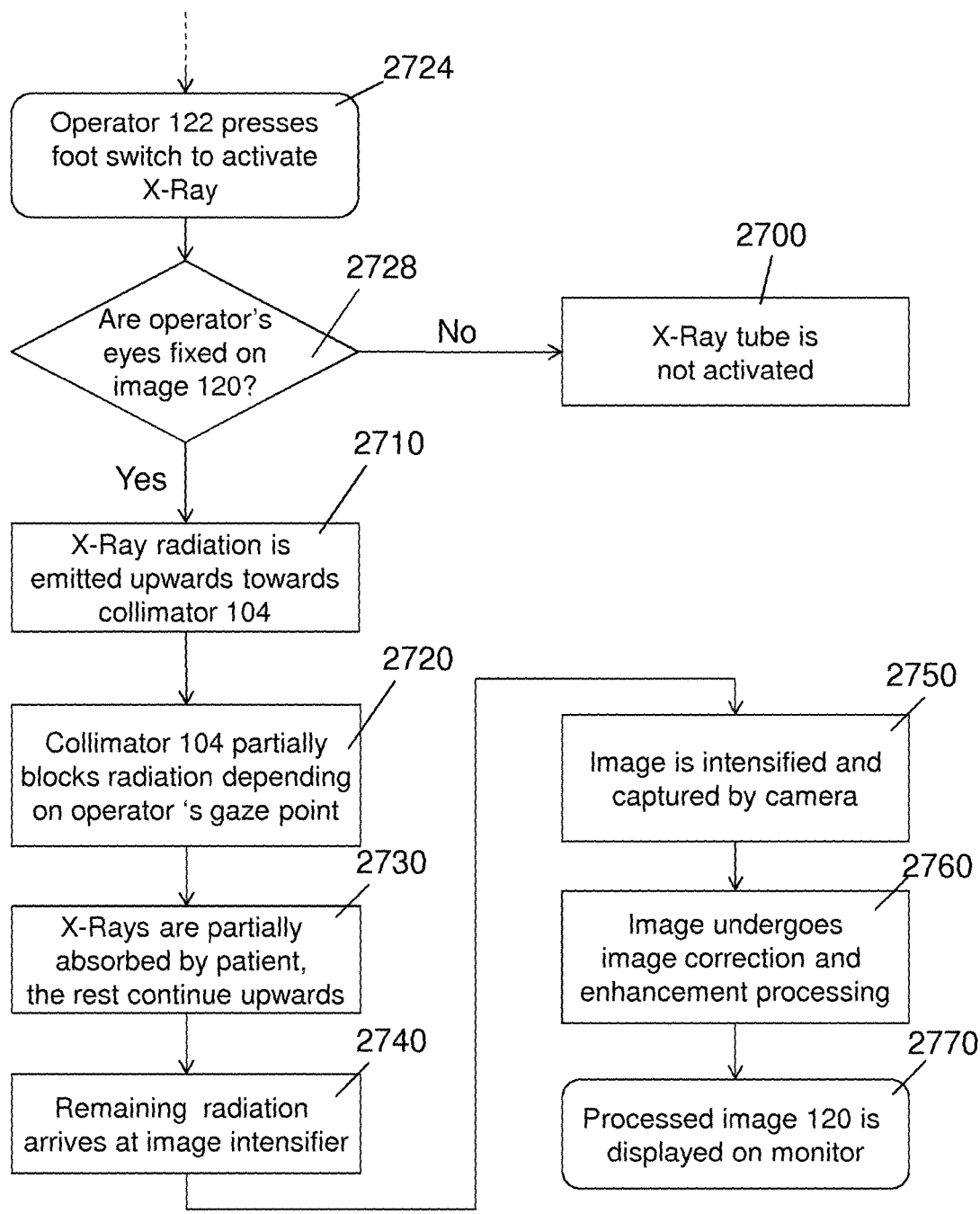
FIG. 21 is a flowchart referencing FIG. 1B, describing the basic fluoroscopy process using an eye tracker.

An example of a more detailed layout of a fluoroscopy clinical environment according to the present invention is described in FIGS. 1B and 21. Operator 122 presses foot switch 124 to activate x-ray (step 2724). Eye tracker 128 (such as EyeLink 1000 available from SR Research Ltd., Kanata, Ontario, Canada) or any alternative input device provides indication where operator 122 is looking (step 2728). This information is typically provided relative to monitor 118. This information, the "gazing point", may be provided for example in terms of (X,Z) coordinates, in the plane of monitor 118, using coordinate system 126. It would be appreciated that in this example the plane of monitor 118 and therefore also image 120 are parallel to the (X,Z) plane of coordinate system 126. Other coordinate systems are possible, including coordinate systems that are bundled to monitor 118 and rotate with monitor 118 when it is rotated relative to coordinate system 126.

The data from input 128 is provided to controller 127 which is basically a computer, such as any PC computer. If the controller 127 determines that the operator's gaze is not fixed on the image 120, the x-ray tube 100 is not activated (step 2700). Otherwise, in step 2710, x-ray tube 100 is activated and x-ray radiation is emitted towards collimator 104

Figure 2:
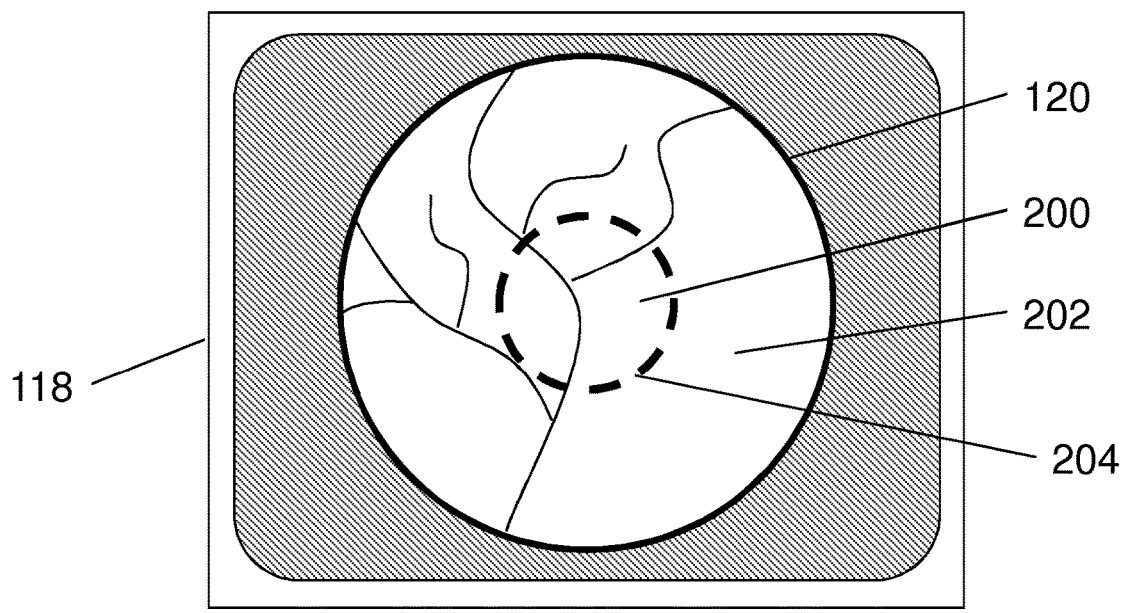
FIG. 2 is a schematic illustration of an example of image displayed on a monitor of a fluoroscopic system.

Reference is made now to FIG. 2 illustrating an example of an image 120 displayed on monitor 118. In this example dashed circle line 204 indicates the border between segment 200 of the image and segment 202 of the image, both segments constitute the entire image 120. In this example it is desired to get a good image quality in segment 200 meaning higher x-ray DPP for segment 200 and it is acceptable to have a lower image quality in segment 202, meaning lower DPP for segment 202.

It would be appreciated that the two segments 200 and 202 are provided here only as one example of an embodiment of the invention that is not limited to this example and that image 120 can be divided to any set of segments by controlling the shape of the apertures in the collimators and mode of motion of the collimators. Such examples will be provided below.

It would be appreciated that DPP should be interpreted as the x-ray dose delivered towards a segment representing one pixel of image 120 to generate the pixel readout value used to construct image 120 (excluding absorption by the patient or other elements which are not a part of the system, such as the hands and tools of the operator).

Figure 3:
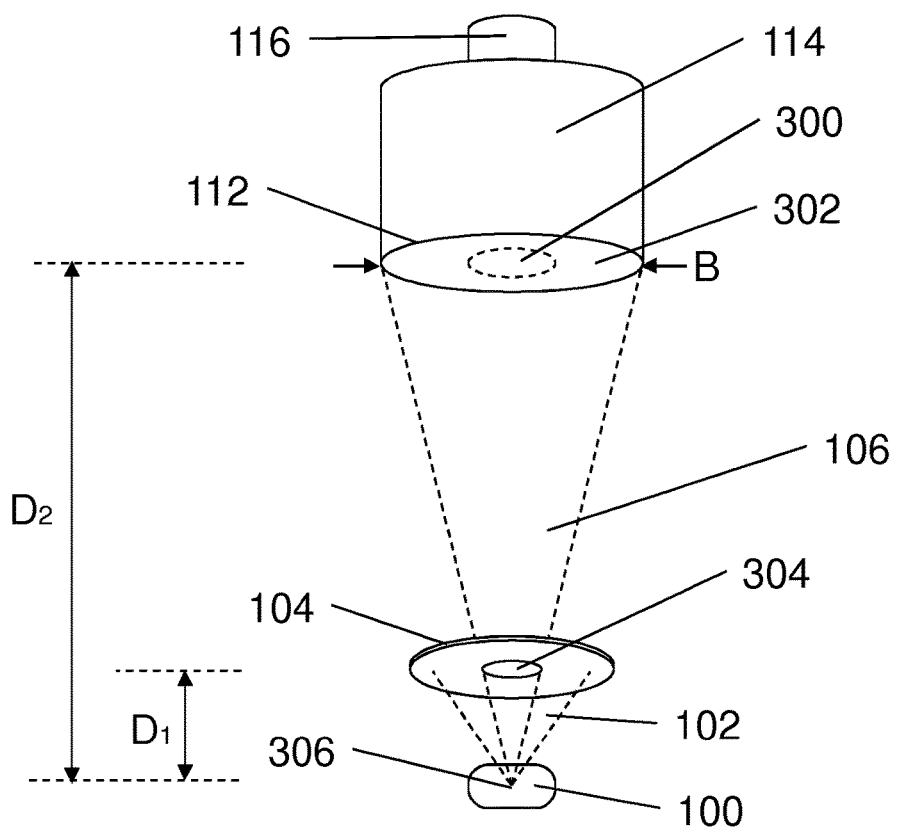
FIG. 3 is a schematic illustration of additional aspects of the system example of FIG. 1A.

Reference is made now to FIG. 3. A typical collimator 104 having a round aperture 304 is introduced to the x-ray path so that only x-rays 106 that are projected from focal point 306 of x-ray tube 100 and pass through aperture 304 arrive at the round input surface 112 of image intensifier 114 while other x-rays 102 are blocked by the collimator. This arrangement exposes the entire input area 112 of the image intensifier to generally the same DPP. Such an arrangement does not provide the function of one DPP to segment 300 that correlates with segment 200 of FIG. 2 and another DPP to segment 302 that correlates with segment 202 of FIG. 2. The diameter of input area 112 is B as indicated in FIG. 3.

D1 represents the distance from the x-ray focal point 306 to aperture 104. D2 represents the distance from the x-ray focal point 306 to image intensifier input surface 112.

Figure 4:
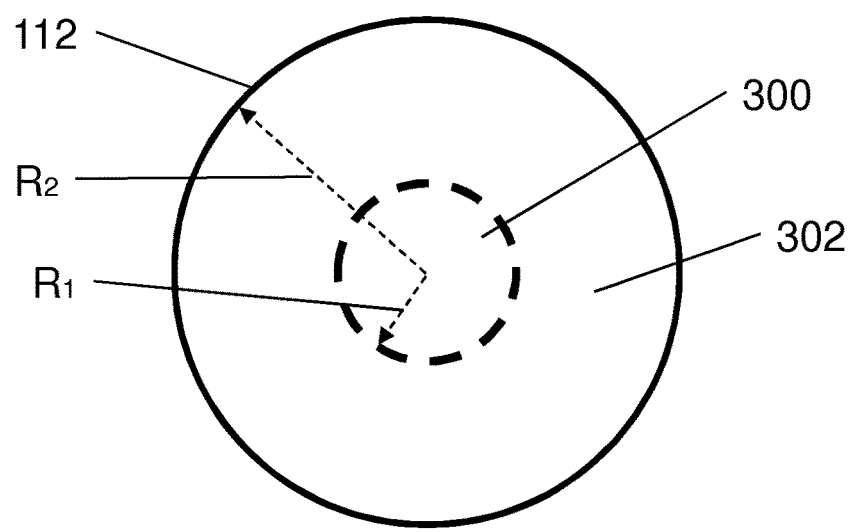
FIG. 4 is a schematic illustration of an example of x-ray exposure regions of the detector in reference to the parameters of FIG. 3.

Reference is made now to FIG. 4 that defined the segments of the current example of the image intensifier input surface 112 to support an example of the invention. In this example segment 300 is a circular area of radius R1 centered on circular input area 112 of the image intensifier. Segment 302 has an annulus shape with internal radius R1 and external radius R2. R2 is also typically the radius of the input area of the image intensifier.

Figure 5:
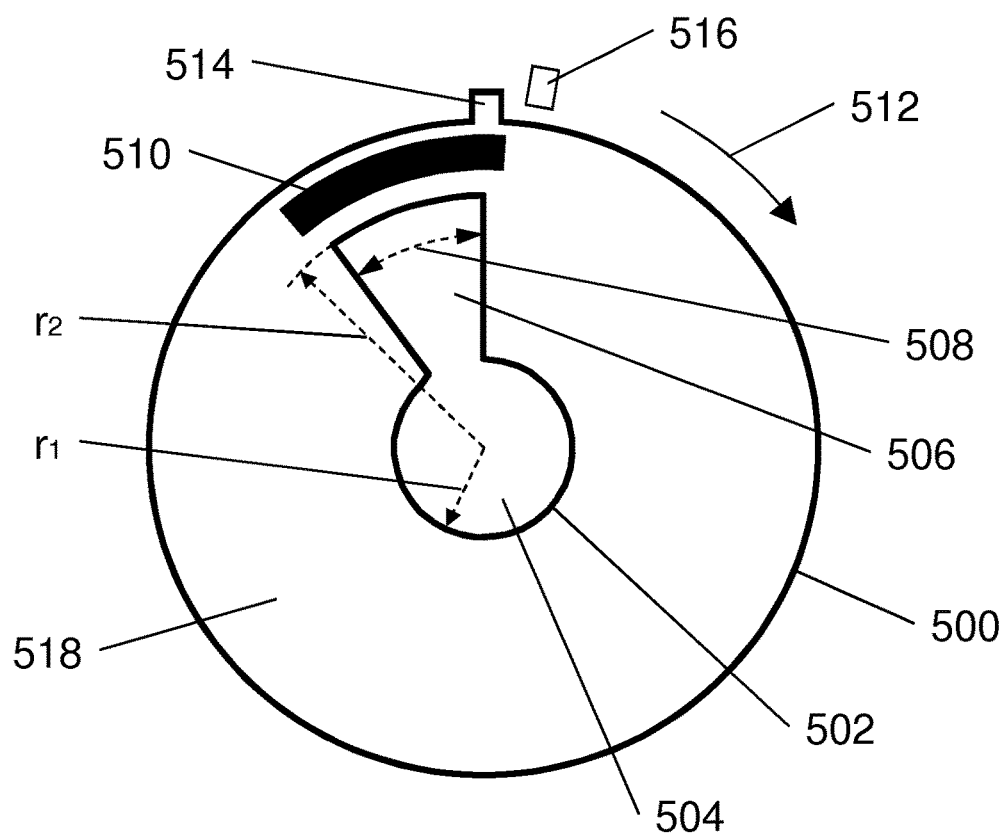
FIG. 5 is a schematic illustration of an example of a collimator according to the present invention.

Reference is made now to FIG. 5 that provides one embodiment of a collimator that functions to provide one DPP for segment 300 and another DPP for segment 302.

Collimator 500 is constructed basically as a round plate of x-ray absorbing material (such as lead, typically 1-4 mm thick), of a radius larger than r2. Aperture 502 of collimator 500 is constructed as a circular cut-out 504 of radius r1 at the center of the collimator and a sector cut-out 506 of radius r2 and angle 508. It would be appreciated that the term sector is used both to indicate a sector of a circular area and a sector of an annulus shaped area, as per the context.

In this example, r1 and r2 of aperture 502 are designed to provide R1 and R2 of FIG. 4. When collimator 500 is positioned in the location of collimator 104 of FIG. 4 r1 and r2 can be calculated using the following equations:

$$r1 = R1/(D2/D1)$$

$$r2 = R2/(D2/D1)$$

In this example angular span 508 is 36 degrees, 1/10 of a circle. Collimator 500 can rotate about its center as shown by arrow 512. Weight 510 can be added to balance collimator 500 and ensure that the center of gravity coordinates in the plane of the collimator coincide with the center of rotation, thus avoiding vibrations of the system that might result from an un-balanced collimator. Following a completion of one 360 degrees rotation, DPP for segment 302 is 1/10 of the DPP of segment 300.

It would be appreciated that angle 508 can be designed to achieve any desired of DPP ratios. For example, if angle 508 will be designed to be 18 degrees, following one complete rotation of aperture 500 the DPP for segment 302 will be 1/20 of the DPP of segment 300. The discussion of the current example will be made in reference to angle 508 being 36 degrees.

Following the completion of one rotation of collimator 500, camera 116 captures one frame of the data integrated by the sensor over the one complete rotation time of collimator 500, such a frame consists of the values read from the set of pixels of the camera sensor. This will described in more details now, providing as an example a camera based on a CCD (charge coupled device) sensor such as TH 8730 CCD Camera available from THALES ELECTRON DEVICES, Velizy Cedex, France.

In this example, synchronization of the camera 116 with collimator 500 rotation is made using tab 514 constructed on collimator 500 that passes through photo-sensor 516 such as EE-SX3070 available from OMRON Management Center of America, Inc., Schaumburg, Ill., U.S.A.

When tab 514 interruption signal is received from photo sensor 516, the lines of camera 116 sensor are transferred to their shift registers and the pixels start new integration cycle. The data of the previous integration cycle is read out from the camera. When tab 514 interrupts photo sensor 516 again, the accumulated signals are transferred again to the shift registers of camera sensor 116 to be read out as the next frame.

Through this method, one frame is generated for each collimator complete round. For each frame the DPP in segment 202 of image 120 is 1/10 the DPP in segment 200 of image 120.

Figure 6:
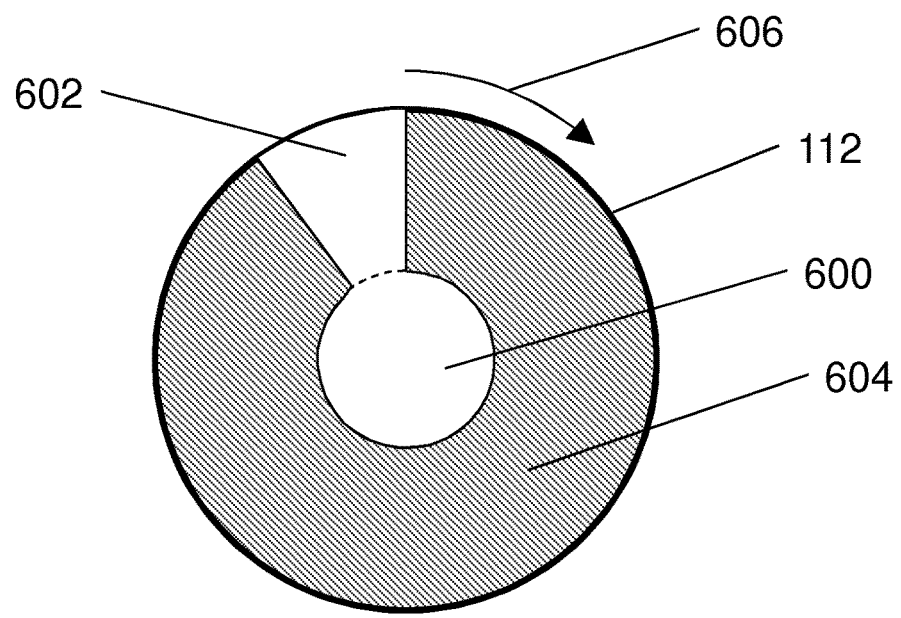
FIG. 6 is a schematic illustration of an example of the exposed region of the image intensifier at a certain rotation angle of the collimator of FIG. 5.
Figure 7:
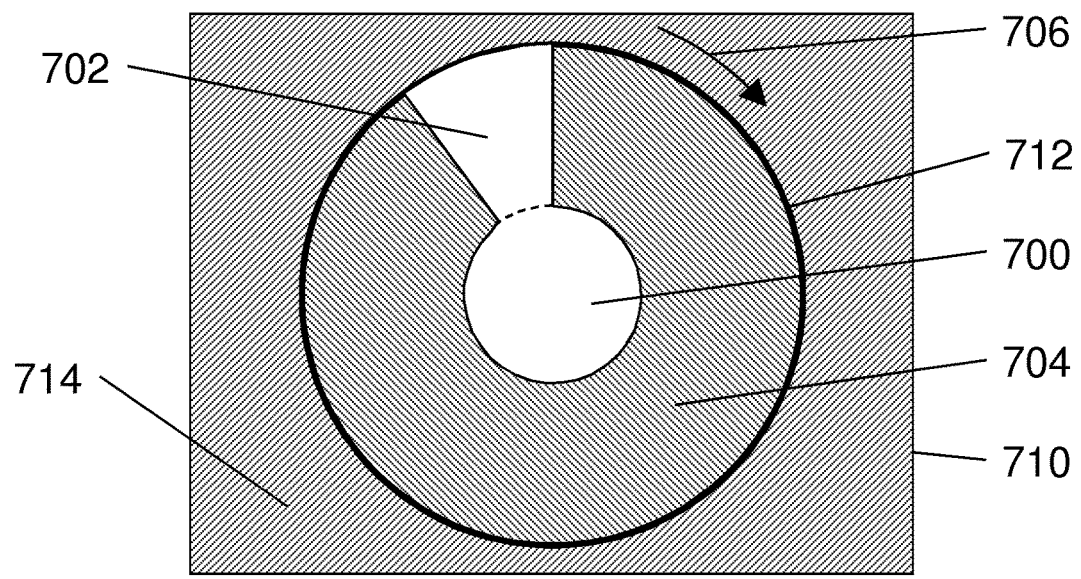
FIG. 7 is a schematic illustration of an example of the light exposure pattern of the sensor at a certain rotation angle of the collimator of FIG. 5.

To provide additional view of the above, reference is made to FIG. 6 that describes the exposure map of image intensifier input 112 at a momentary position of the rotating collimator 500. In this position circular area 600 and sector area 602 are exposed to radiation while the complementary sector 604 is not exposed to radiation being blocked by collimator 500. As collimator 500 rotates, sector area 602 and 604 rotate with it while circular area 600 remains unchanged. During one cycle of constant speed of rotation of collimator 500, each pixel outside of area 600 is exposed to x-ray fro 1/10 of the time of a pixel in area 600 and thus, receives DPP that is 1/10 than a pixel of area 600. In FIG. 7 the equivalent optical image projected on the camera sensor 710 is shown, where area 700 of FIG. 7 is the equivalent of area 600 of FIG. 6, area 702 of FIG. 7 is the equivalent of area 602 of FIG. 6. The output image of image intensifier projection on sensor 710 is indicated by numerical indicator 712. 714 is a typical sensor area that is outside the range of the image intensifier output image.

For each frame, in addition to typical offset and gain correction to compensate per pixel linear response characteristics, a multiplication by a factor of 10 of the signal from pixels of segment 202 would be needed to generate an image 120 so that the brightness and contrast appearance of segment 202 would be similar to that of segment 200. This method described here in reference to a specific example will be called "normalization" of the pixels. Normalization scheme is made in accordance to the x-ray exposure scheme (i.e., collimator shape, speed and position).

To generate a cine of 10 frames per second (fps) collimator 500 has to be rotated as a speed of 10 rounds per second (rps). To generate a cine of 16 fps collimator 500 has to be rotated as a speed of 16 rps.

With each such rotation of 360 degrees a complete exposure of input area 112 is completed. An Exposure Cycle (EC) is therefore defined to be the smallest amount of rotation of collimator 500 to provide the minimal complete designed exposure of input area 112. In the example of collimator 500 of FIG. 5, EC requires a rotation of 360 degrees. For other collimator designs such as the one of FIG. 13A EC requires 180 degrees rotation and the one of FIG. 13B EC requires 120 degrees rotation.

It would be appreciated that the examples of collimators, x-ray projections on image intensifier input area 112, the images projected on the camera sensor (or flat panel sensor) and the images displayed on monitor 118 are described in a general way ignoring possible geometrical issues such as image up-side down due to lens imaging that might be different if a mirror is also used or the direction of rotation that is shown clockwise throughout the description but depending on the specific design and orientation of the observer might be different. It is appreciated that a person skilled in the art understands these options and has the proper interpretation for any specific system design.

It would be appreciated that the camera frames reading scheme described above in reference to collimator 500 can be different:
1. The reading of the frame does not have to be at the instant that tab 514 interrupts photo sensor 516. This can be done at any phase of collimator 500 rotation as long as it is done at the same phase for every EC.
2. Reading more than one frame during one EC. It is desired however, that for each EC, an integer number of frames will be read. By doing so, the read frames include the complete data of one EC which makes it easier to build one display-frame that can be presented on monitor 118 in few ways:
   a. Sum up the pixel values of all the frames of one EC to generate one complete exposure image. Then sum up the pixel values of all the frames of the next EC to generate next complete exposure image. This way, the picture on the monitor is replaced by a temporally successive image each time an EC is completed. Normalization of pixel values can be made for each frame separately or once only for the sum of the frames, or any other combination of frames.
   b. For the example of this method lets assume that the camera provides 8 frames during one EC. In this example, all 8 frames numbered 1 to 8 are stored in frames storage and a first display-frame is generated from these frames as described above (summing the frames and normalizing pixel values). The resultant image is then displayed on monitor 118. When frame 9 is acquired (after 1/8 EC), frame 1 is replaced by frame 9 in the frames storage and frames 9,2,3,4,5,6,7,8 are processed (summing, normalizing) to generate the second display-frame that can now be displayed on monitor 118 after 1/8 EC. After another 1/8 of an EC frame 10 is acquired and stored in position of frame 2. Frames 9,10,3,4,5,6,7,8 are now processed to generate the third display-frame. This way, using a frames storage managed in the method of FIFO (first in first out) and generating display-frames with each new frame acquired from the sensor, a sequence of cine images are displayed for the user on monitor 118.
   c. In another embodiment of the invention, summing the pixels of frames is made only for pixels that have been exposed to x-ray according to the criteria of collimator shape and motion during the integration time of the acquired frame. In example b above this would be 1/8 of the EC time. The pixels to be summed to create the image are (1) those from area 700 and (2) those in a sector of angle in the order of 2×(the angular span 508 of the collimator sector 506). The reason for 2λ is that during 1/8 of the integration time the collimator rotates 1/8 of EC. A sector angle somewhat larger than 2·(angle 508) might be desired to compensate for accuracy limitations. This summing method reduces considerably the amount of pixels involved in the summing process and thus reduces calculation time and computing resources.
   d. In another embodiment of the invention, the pixel processing is limited to those pixels specified in c above. This processing method reduces considerably the amount of pixels involved in the processing and thus reduces calculation time and computing resources.
   e. In another embodiment of the invention, the storing of pixels is limited to those pixels specified in c above. This storing method reduces considerably the amount of pixels involved in the storage and thus reduces storage needs.

f. In another embodiment of the invention, any of the methods described in this section (a—as a general concept, b—as a specific example of a, c, d and e) can be combined to an implementation that uses any combination of the methods or few of them.

3. Reading one frame during more than one EC. In yet another embodiment, the collimator can be operated to provide an integer number of EC per one frame received from the sensor. For example, after 2 EC made by the collimator, one frame is read from the sensor. After normalizing pixel values of this frame, it can be displayed on monitor 118.

It would be appreciated that in many designs the frame rate provided from the sensor is dictated by the sensor and associated electronics and firmware. In such cases the speed of rotation of collimator 500 can be adjusted to the sensor characteristics so that one EC time will be the same as the time of receiving an integer number of frames from the sensor (one frame or more). It is also possible to set the rotation speed of the collimator so that an integer number of EC will be completed during the time cycle for acquiring on frame from the sensor.

The description of frames reading above is particularly adequate to CCD like sensors, whether CCD cameras mounted on image intensifier or flat panel sensors used instead of image intensifiers and cameras and located generally at plane 112 of FIG. 3. The specific feature of CCD is capturing the values of the complete frame, all the pixels of the sensor, at once. This is followed by sequential transfer of the analog values to an analog to digital convertor (ND). Other sensors such as CMOS imaging sensors read the frame pixels typically one by one in what is known as a rolling shutter method. The methods of reading the sensor frames in synchronization with the collimator EC is applicable to such sensors as well regardless of the frames reading methods. The "random access" capability to read pixels of sensors such as CMOS sensors provides for yet another embodiment of the present invention. Unlike a CCD sensor, the order of reading pixels from a CMOS sensor can be any order as desired by the designer of the system. The following embodiment uses this capability. In this context, CMOS sensor represents any sensor that supports pixel reading in any order.

Figure 8:
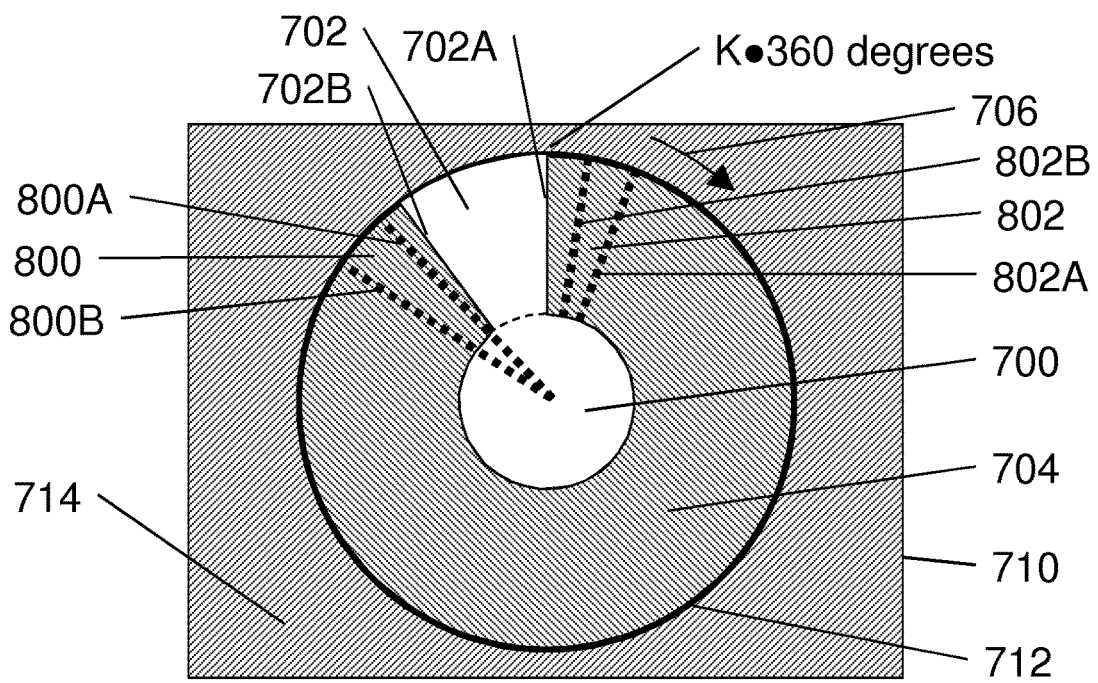
FIG. 8 is a schematic illustration of an example of reading process of pixel values of the sensor.

Reference is made now to FIG. 8. The embodiment of FIG. 8 is also described using an example of image intensifier and a CMOS camera but it would be appreciated that the method of this embodiment is applicable also to flat panel sensors and other sensors capable of random access for pixel reading.

The output image of image intensifier 114 is projected on area 712 of sensor 710. In accordance to the momentary position of rotating collimator 500, circle 700 and sector 702 are momentary illuminated in conjunction with collimator 500 position and sector 704 and sector 714 are not illuminated. Sectors 702 and 704 rotate as shown by arrow 706 in conjunction with the rotation of collimator 500.

For the purpose of this example, pixels before a radial line such as 702A or 800A are pixels which their centers are on the radial line or in direction clockwise from the radial line. Pixels that are after the radial line are pixels with centers that are in direction anticlockwise from the radial line. Sector 702 for example includes pixels that are after radial line 702A and also before radial line 702B. For example, in an embodiment mode where frame is read from the sensor once in an EC, the pixels adjacent to radial line 702A have just started to be exposed to the output image of the image intensifier and pixels adjacent to radial line 702B have just completed to be exposed to the output image of the image intensifier. Pixels in sector 702 are partially exposed per their location between 702A and 702B. In this example, the pixels in sector between radial lines 702B and 800B has not been read yet after being exposed to the image intensifier output.

In the current example of this embodiment, the instant angular position of radial line 702A is K·360 degrees (K times 360, K is an integer indicating the number of EC from the beginning of rotation). Angular span of section 702 is 36 degrees per the example of collimator 500. Therefore radial line 702B is at angle K·360−36 degrees. At this position of the collimator, a reading cycle of the pixels of sector 800 starts. Radial line 800A is defined to ensure that all pixels after this radial line have been fully exposed. This angle can be determined using R1 of FIG. 5 and the pixel size projected on FIG. 5. To calculate a theoretical minimum angular gap between 702B and 800A to ensure that also the pixels adjacent to 800A have been fully exposed one should consider an arch of radius R1 in the length that has a chord of ½ pixel diagonal in length. This determines the minimum angular span between 702B and 800A to ensure full exposure to all the pixels in sector 800. In a more practical implementation, assuming that area 712 is about 1,000 pixels vertically and 1,000 pixels horizontally, and that R1 is in the order of ¼÷½ of R2 (see FIG. 4) and considering tolerances of such designs and implementation, a useful arch length of radius R1 would be, for example, the length of 5 pixels diagonal. This means the angular span between 702B and 800A will be about 2.5 degrees. That is, at the instant of FIG. 8 the angular position of radial line 800A is K·360−(36+2.5) degrees.

In this specific example of the present embodiment, the angular span of sector 800 is also selected to be 36 degrees. Therefore, at the instant of FIG. 8 the angular position of radial line 800B is K·360−(36+2.5+36) degrees.

In FIG. 8 the angular span of sector 800 is drawn to demonstrate a smaller angle then the angular span of sector 702 to emphasize that the angles need not to be the same and they are the same in the example provided here in the text just for the purpose of the specific example of the embodiment.

Having determined the geometry of sector 800, the pixels of that sector are read now from the camera sensor. In a typical CMOS sensor the reading of each pixel is followed by a reset to that pixel so that the pixel can start integration signal from zero again. In another embodiment, in a first phase all the pixels of sector 800 are readout and in a second phase the pixels are reset. The reading and reset cycle of sector 800 has to be finished within the time it takes to sector 702 rotate an angular distance equal to the angular span of sector 800 to enable the system to be ready on time to read the next sector of the same angular span as sector 800 but is rotated clockwise the amount of angular span of sector 800 relative to the angular position of sector 800. In this example: 36 degrees.

In the above example, with collimator 500 is rotating at 10 rps, sector 800 of 36 degrees span will assume 10 orientations through one EC, the orientations are 36 degrees apart and pixel reading and resetting cycles will be made at a rate of 10 cps (cycles per second).

It would be appreciated that this embodiment can be implemented in different specific designs.

For example, the angular span of sector 800 might be designed to 18 degrees while that of sector 702 is still 36 degrees and collimator 500 is rotating at 10 rps.

In this example, sector 800 will assume 20 orientations through one EC, the orientations are 18 degrees apart and pixel reading and resetting cycles will be made at a rate of 20 cps (cycles per second).

In yet another embodiment, the dark noise accumulated by the pixels in sector 704 that are after radial line 800B and before radial line 802A is removed by another reset cycle of the pixels located in sector 802 (after radial line 802A and before radial line 802B). This reset process is ideally made in a sector 802 specified near and before sector 702. The reset of all pixels of sector 802 has to be completed before radial line 702A of rotating sector 702 reaches pixels of sector 802. Otherwise, the angular span and angular position of reset sector 802 are designed in methods and considerations analog to those used to determine sector 800.

Pixels read from sector 800 should be processed for normalization and can be used to generate display-frames in ways similar to those described in section 2 above "Reading more than one frame during one EC" where in the current embodiment only the sector pixels are read, stored and processed and not the complete sensor frame.

In this embodiment, after pixel normalization of the last sector read, the processed pixels can be used to replace directly the corresponding pixels in the display-frame. This way the display-frame is refreshed in a mode similar to a radar beam sweep, each time the next sector of the image is refreshed. Following 360/(angular span of the readout sector) refreshments, the entire display-frame is refreshed. This provides a simple image refreshment scheme.

Figure 9:
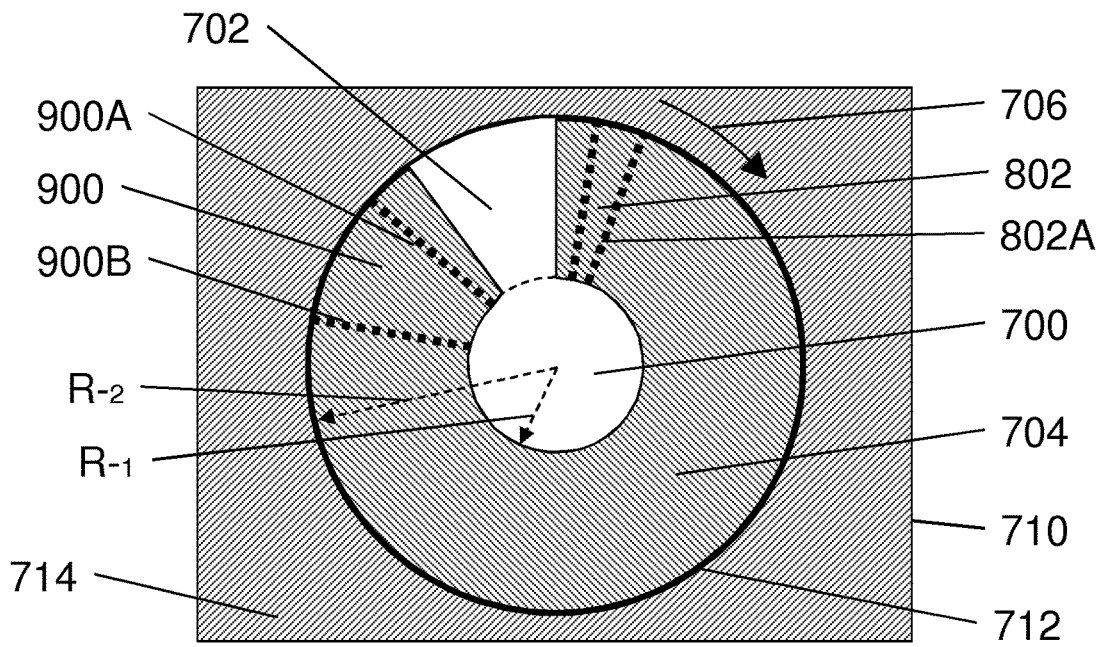
FIG. 9 is a schematic illustration of an example of reading process of pixel values of the sensor.

Attention is made now to FIG. 9. Unlike FIG. 8 where the reading sector included the complete set of pixels located after radial line 800A and before radial line 800B, in the present invention the reading area geometry is divided to two parts: circular area 700 and sector 900. Sector 900 of the embodiment of FIG. 9 contains the pixels that are after radial line 900A and are also before radial line 900B and are also located after radiuses R-1 and before R-2. In this example pixels before a radius are those with distance from the center smaller or equal to radius R and pixels after a radius R are those with distance from the center larger then R. The pixels of area 700 are all those pixels located before R-1.

In this embodiment, the pixels of section 900 are read and handled in using the same methods described in reference to the embodiment of FIG. 8. The same holds also for reset sector 802.

The pixels of area 700 are handled differently.

In one implementation of the current embodiment, The pixels in area 700 can be read once or more during one EC and handled as described above for the embodiment of reading the entire CMOS sensor or area 700 can be read once in more than one EC and handled accordingly as described above for the embodiment of reading the entire CMOS sensor.

It would be appreciated that for each reading method the normalization process of the pixels must be executed to get a display-frame where all the pixels values represents same sensitivity to exposure.

Attention is made now to FIG. 10 that provides one example for the design of a collimator of the present invention combined with a motion system aimed to provide the rotation function of collimator 500.

Figure 10A:
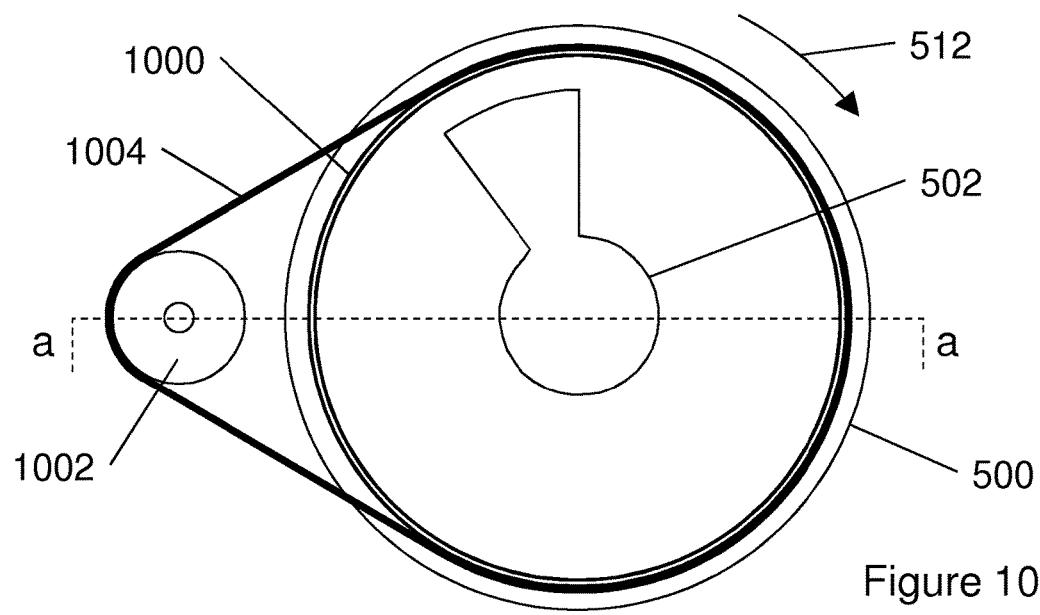
FIG. 10A is a schematic illustration of a top view of an example of a collimator of the invention.

FIG. 10A is a top view of the collimator and the rotation system of this example.

Figure 10B:
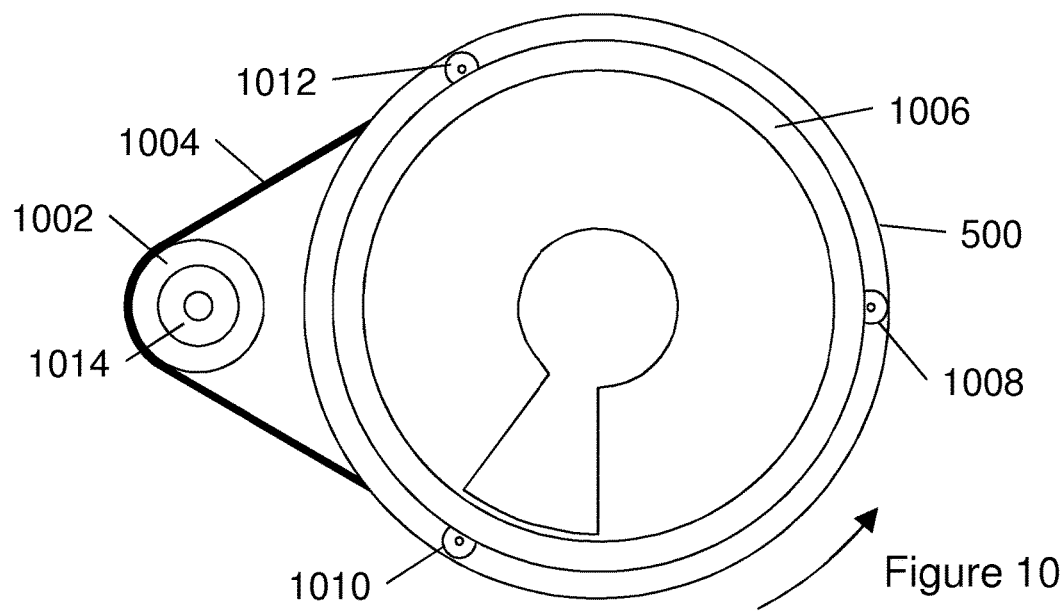
FIG. 10B is a schematic illustration of a bottom view of the example collimator of FIG. 10A.

FIG. 10B is a bottom view of the collimator and the rotation system of this example.

Figure 10C:
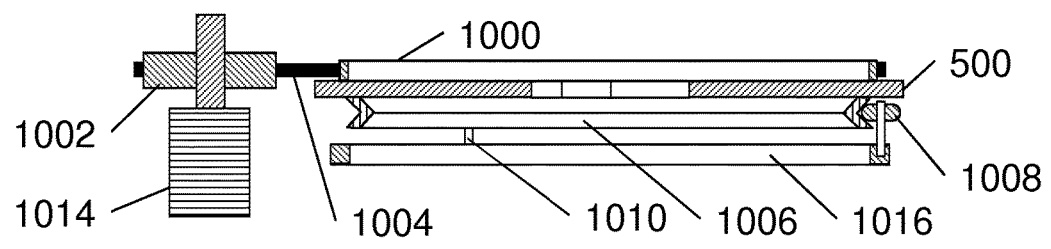
FIG. 10C is a schematic illustration of a cross-section view of the example collimator of FIG. 10A.

FIG. 10C is a view of cross-section a-a of FIG. 10A.

FIG. 10A is showing collimator 500 and aperture 502 (other details are removed for clarity). Pulley 1000 is mounted on top of collimator 500 in a concentric location to the collimator. Pulley 1002 is mounted on motor 1012 (see motor in FIG. 10B and FIG. 10C). Belt 1004 connects pulley 1000 with pulley 1002 to transfer the rotation of pulley 1002 to pulley 1000 and thus to provide the desired rotation of collimator 500. The belt and pulley system example 1000, 1002 and 1004 presents a flat belt system but it would be appreciated that any other belt system can be used including round belts, V-belts, multi-groove belts, ribbed belt, film belts and timing belts systems. FIG. 10B showing the bottom side of FIG. 10A displays more components not shown before. V-shape circular track 1006 concentric with collimator 500 is shown (see a-a cross section of 1006 in FIG. 10C). Three wheels 1008, 1010 and 1012 are in contact with the V-groove of track 1006. The rotation axes of the 3 wheels are mounted on an annulus shaped static part 1016 (not shown in FIG. 10B) that is fixed to the reference frame of the x-ray tube. This structure provides a support of collimator 500 in a desired position in reference to the x-ray tube (for example the position of collimator 104 of FIG. 3) while, at the same time provides 3 wheels 1008, 1010 and 1012 with track 1006 for collimator 500 to rotate as desired.

The rotation of motor 1014 is transferred to collimator 500 by pulley 1002, through belt 1004 and pulley 1006. Collimator 500 then rotates being supported by track 1006 that slides on wheels 1008, 1010 and 1022.

It would be appreciated that the rotation mechanism described here is just one example for a possible implementation of rotation mechanism for a rotating collimator. Rotation mechanism might instead use gear transmission of any kind including spur, helical, bevel, hypoid, crown and worm gears. The rotation mechanism can use for 1002 a high friction surface cylinder and bring 1002 in direct contact with the rim of collimator 500 so that belt 1004 and pulley 1000 are not required. Another implementation may configure collimator 500 as also a rotor of a motor with the addition of a stator built around it.

In the description of the collimator of FIG. 5, tab 514 and photo sensor 516 were presented as elements providing tracing of the angular position of collimator 500 for the purpose of synchronization between the collimator angular position and the sensor reading process. These elements were presented as one implementation example. The embodiment means for tracing the rotational position can be implemented in many other ways. In the example of FIG. 10, motor 1002 might have a attached encoder such as available from Maxon Precision Motors, Inc, Fall River, Mass., USA. Simple encoder can be constructed by taping a black and white binary coded strip to the circumference of collimator 500 and reading the strip using optical sensors such as TCRT5000 Reflective Optical sensor available from Newark, http://www.newark.com.

Collimator 500 was described hereinabove as having a fixed aperture that can not be modified after manufacturing of the collimator.

It would be appreciated that in other embodiment of the inventions, mechanical designs of collimator assemblies can be made to accommodate exchangeable collimators. This way, different apertures can be mounted to the collimator assembly per the needs of the specific application.

In additional implementation example of the invention, the collimator can be designed to have a variable aperture within the collimator assembly. This is demonstrated in reference to FIG. 11.

Figure 11A:
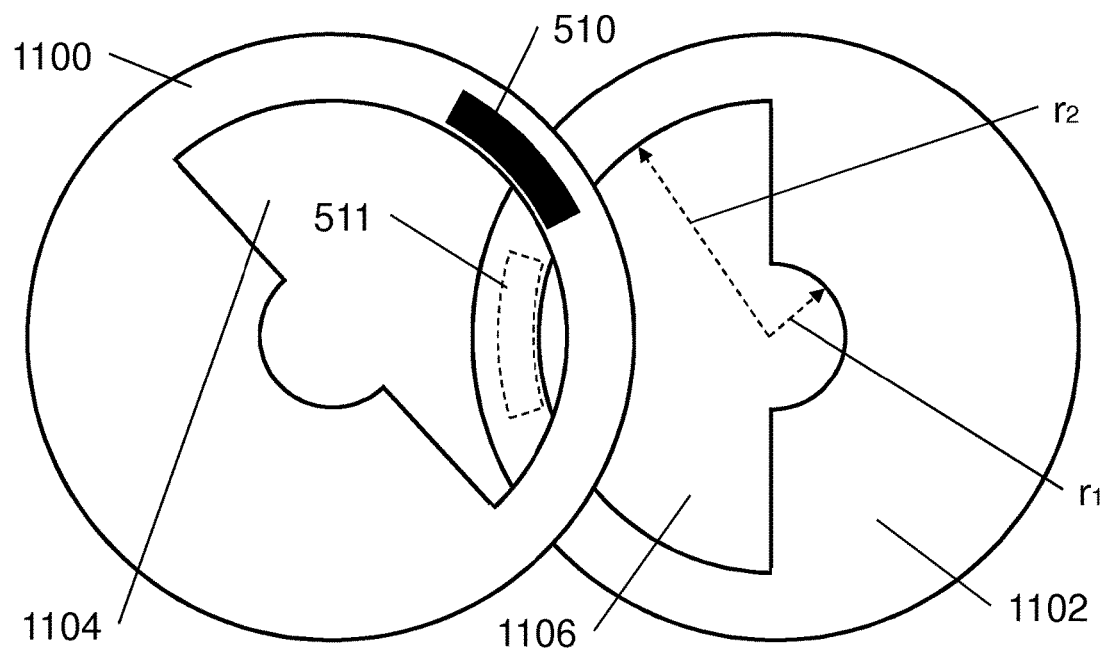
FIG. 11A is a schematic illustration of the main parts of another example of a collimator of the invention.

The collimator of FIG. 11 is constricted from two superimposed collimators shown in FIG. 11A. One collimator is 1100 with aperture 1104 and balancing weight 510 to bring the center of gravity of this collimator to the center of rotation of this collimator. The second collimator is 1102 with aperture 1105 and balancing weight 511 to bring the center of gravity of this collimator to the center of rotation of this collimator. In both collimators the aperture geometry is the combination of central circular hole of radius r1 and sector hole of radius r2 and sector angular span of 180 degrees. Actually, collimator 1102 is of the same general design as collimator 1100 and it is flipped upside down.

Figure 11B:
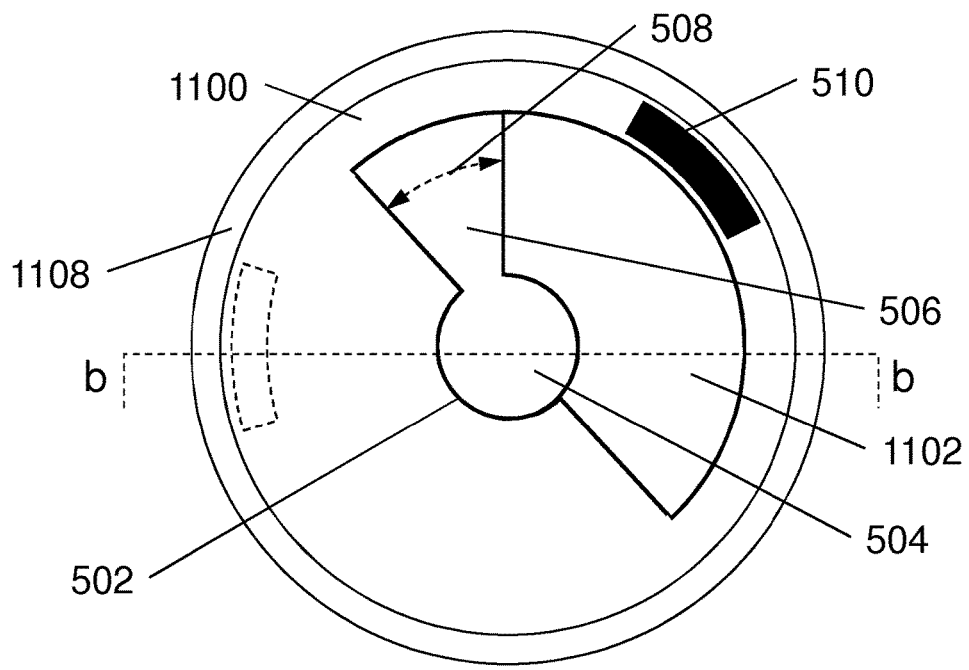
FIG. 11B is a schematic illustration of the parts of FIG. 11A in the operative configuration.
Figure 11C:
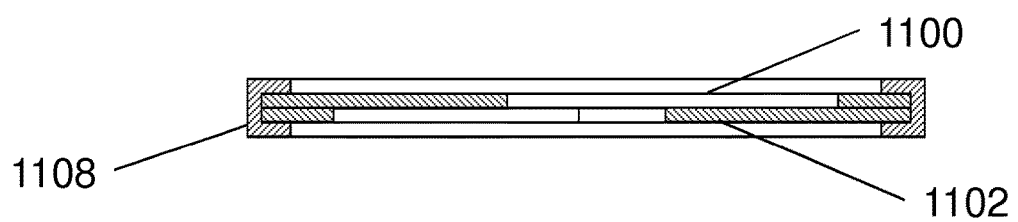
FIG. 11C is a schematic illustration of a cross section of FIG. 11B.
Figure 11D:
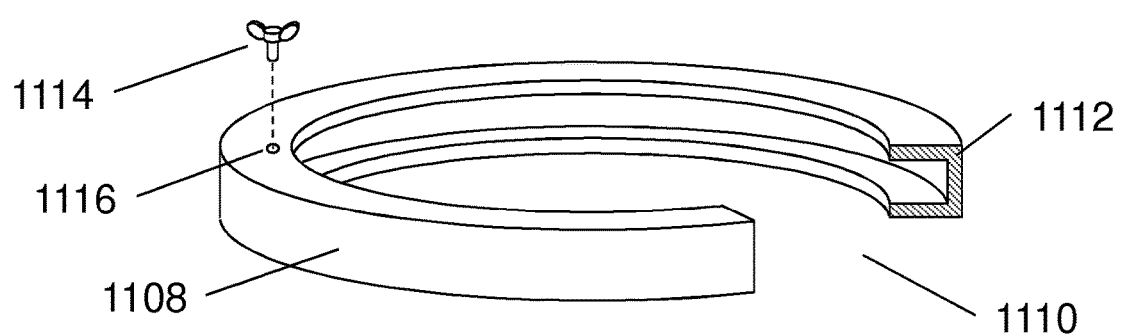
FIG. 11D is a schematic illustration of parts of the collimator example of FIG. 11B.

When collimators 110 and 1102 are placed concentric one on top of the other as shown in FIG. 11B we get a combined aperture which is the same as that in collimator 500 of FIG. 5. By rotating collimator 1100 relative to collimator 1102, the angular span of sector 508 can be increased or decreased. In this example the angular span of sector 508 can be set in the range of 0÷180 degrees. In this example, ring 1108 holds collimators 1100 and 1102 together as shown also in FIG. 11C which is cross-section b-b of FIG. 11B. Reference is made to FIG. 11C now (weights 510 and 511 are not shown in this cross-section drawing). In this example of the invention, ring 1108 is shown holding together collimators 1100 and 1102, allowing them to be rotated one relative to the other to set the angular span 508 of sector 506 as desired. An example for a locking mechanism to hold collimators 1100 and 1102 is the relative desired orientation is described in FIG. 11D. In FIG. 11D ring 1108 is shown without collimators 1100 and 1102 for clarity. A section 1110 is cut-out in the drawing to expose the u-shape 1112 of ring 1108, inside which collimators 1100 and 1102 are held. Screw 1114 that fits into threaded hole 1116 is used to lock collimators 1100 and 1102 in position after the desired angular span 508 has been set. To change angular span 508 the operator can release screw 1114, re-adjust the orientation of collimators 1100 and/or 1102 and fasten screw 1114 again to set the collimators position. The example of FIG. 11, including the manual adjustment of angular span 508 is provided as one example of implementation of the invention. Many other options are available. One more example is shown in reference to FIG. 12. In this example, angular span 508 can be controlled by a computer. The mechanism of FIG. 12 is manly a structure containing two units similar to the unit of FIG. 10 with few changes including the removal of pulley 1000 using instead the rim of the collimator as a pulley. Balance weights 510 and 511 are not shown here for clarification of the drawing.

Figure 12A:
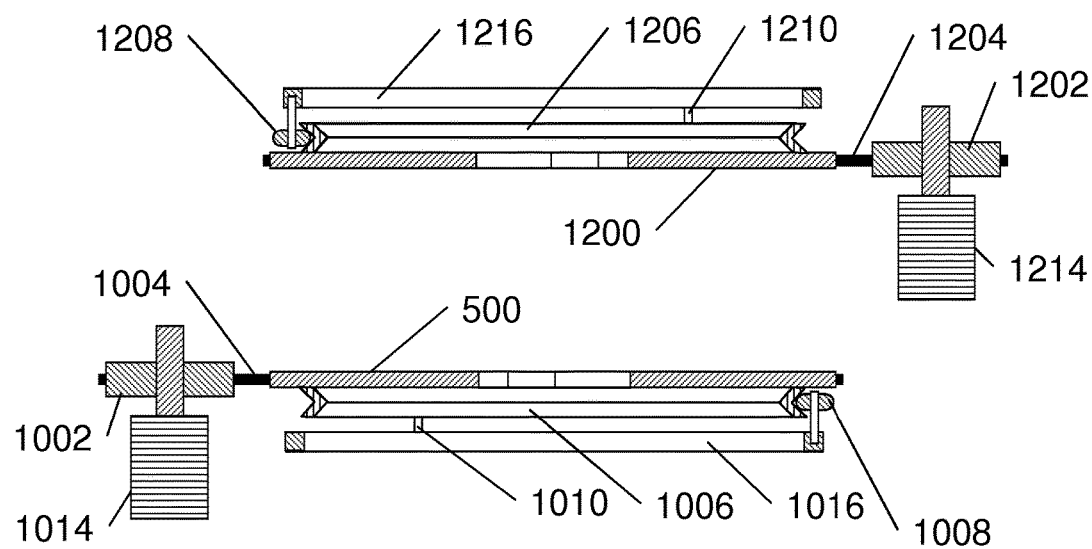
FIG. 12A is a schematic illustration of the main modules of another example of a collimator of the invention.
Figure 12B:
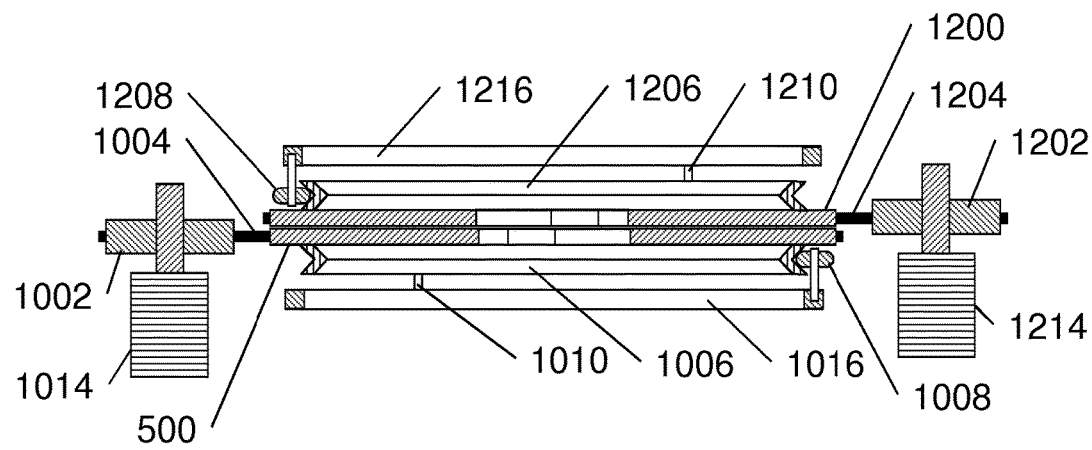
FIG. 12B is a schematic illustration of the modules of FIG. 12A in the operative configuration.

In FIG. 12A, the bottom unit that includes collimator 500 is essentially the assembly of FIG. 10 with pulley 1000 removed and using instead the rim of the collimator 500 as a pulley. In the top unit that includes collimator 1200, the assembly is same as the bottom assembly when the bottom assembly is rotated 180 degrees about an axis vertical to the page with the exception that motor 1214 was rotated another 180 degrees so that it is below the pulley, same as motor 1014. This is not a compulsory of this example but in some design cases it might help to keep the space above the assembly of FIG. 12 clear of unwanted objects. FIG. 12B is showing now these 2 assemblies brought together so that collimators 500 and 1200 are near each other and concentric. In the assembly of FIG. 12B each of the collimators 500 and 1200 can be rotated independently. For each collimator the angular position is known through any encoding system, including the examples provided above. In one example of usage of the assembly of FIG. 12B, angular span 508 is set when collimator 500 is at rest and collimator 1200 is rotated until the desired angle 508 is reached. Then both collimators are rotated at the same speed to provide the x-ray exposure pattern examples as described above. It would be appreciated that it is not required to stop any of the collimators to adjust angle 508. Instead, during the rotation of both collimators, the rotation speed of one collimator relative to the other can be changed until the desired angle 508 is achieved and then continue rotation of both collimators at the same speed.

It would be appreciated that a mechanism with capabilities such as the example of FIG. 12B can be used to introduce more sophisticated exposure patterns. With such mechanisms angle 508 can be changed during an EC to generate multiple exposure patterns. For example angle 508 might be increased for the first half of the EC and decreased for the second half of the EC. This will create an exposure pattern of 3 different exposures (it is appreciated that the borders between the areas exposed through sector 506 will not be sharp and the width of these borders depend on angle 508 and the speed of changing this angle relative to the speed of rotation of the collimators.

It would also be appreciated that any of the collimators of the invention can be rotated at a variable speed through the EC and affect the geometry of exposure. For example, collimator 500 of FIG. 5 can rotate at one speed over the first 180 degrees of the EC and twice as fast during the other 180 degrees of the EC. In this example the area exposed through sector 506 during the first half of the EC will have twice the DPP than the area exposed through sector 506 during the second half of the EC, with gradual DPP change over the boundary between these two halves. The central area exposed through circular aperture 504 will have a $3^{rd}$ level of DPP. Other rotation speed profiles can generate other exposure geometries. For example 3 different rotation speeds over 3 different parts of the EC will generate 4 areas with different DPP.

The examples provided above presented collimators with apertures having similar basic shapes consisting of central round opening combined with a sector-shaped opening. These examples were used to present many aspects of the invention but the invention is not limited to these examples.

Reference is made now to FIG. 13A showing another example of an aperture of the invention. In this example the aperture of collimator 1300 is constructed of a circular hole 1302 concentric with the collimator rim, a sector-shaped hole 1304 and a sector shaped hole 1306 in opposite direction to 1304 (the two sectors are 180 degrees apart). If it is desired, for example that annulus area of FIG. 6 (that includes sectors 602 and 604) will be exposed to DPP that is 1/10 than the DPP of area 600 of FIG. 6 then each of the sectors 1304 and 1306 can be set to 18 degrees and then one EC can be achieved with only 180 degrees rotation of collimator 1300 comparing to 360 degrees required for the collimator of FIG. 5. Also, for 10 fps the rotation speed of collimator 1300 should be 5 rps and not 10 rps as in the case of collimator 500 of FIG. 5. Furthermore, balance weight such as 510 of FIG. 5 is not required for collimator 1300 of FIG. 13A since it is balanced by its' geometry.

Another example of a collimator according to the invention is provided in FIG. 13B. The aperture of collimator 1310 is constructed of a circular hole 1312 concentric with the collimator rim, a sector-shaped hole 1314, a sector-shaped hole 1316 and a sector shaped hole 1318 the three sectors are 120 degrees apart. If it is desired, for example that annulus area of FIG. 6 (that includes sectors 602 and 604) will be exposed to DPP that is 1/10 than the DPP of area 600 of FIG. 6 then each of the sectors 1314, 1316 and 1318 can be set to 12 degrees and then one EC can be achieved with only 120 degrees rotation of collimator 1310 comparing to 360 degrees required for the collimator of FIG. 5. Also, for 10 fps the rotation speed of collimator 1300 should be 10/3 rps and not 10 rps as in the case of collimator 500 of FIG. 5. Furthermore, balance weight such as 510 of FIG. 5 is not required for collimator 1310 of FIG. 13B since it is balanced by its' geometry.

It would be appreciated that relations and methods for rotating the collimator examples of FIG. 13A and FIG. 13B and reading pixel values from the image sensor describe above in relation to the collimator example of FIG. 5 are fully implantable with the examples of the collimators of FIG. 13A and FIG. 13B with adjustments that are obvious for a person skilled in the art. For example, for the collimator of FIG. 13B and a CMOS camera pixel reading sector 800 of FIG. 8 can be complemented by additional 2 pixel reading sectors, each in conjunction to one of the 2 additional aperture sectors of FIG. 13B.

Some of these changes and comparison are indicated in the following table that presents an example of differences in features and implementation between the 3 different examples of collimators.

| Collimator | FIG. 5 | FIG. 13A | FIG. 13B | Comments |
|---|---|---|---|---|
| Central round aperture | Yes | Yes | Yes | |
| # of aperture sectors | 1 | 2 | 3 | |
| Sectors angular span | 36 deg | 18 deg | 12 deg | For 1:10 DPP ratio |
| Sectors angular separation | NA | 180 deg | 120 deg | |
| EC rotation | 360 deg | 180 deg | 120 deg | |
| rps | 10 | 5 | 10/3 | For 10 fps |
| fps at 10 rps | 10 | 20 | 30 | |

FIG. 11 and FIG. 12 provides and example on how collimator 500 of FIG. 5 can be contracted in a way that enables variable angle span 508 of sector 506.

FIG. 14 provides an example how the collimator of FIG. 13A can be constructed so that the angle span of sectors 1304 and 1306 can be adjusted as desired.

In FIG. 14A presents an example of 2 collimators 1400 and 1402. The gray background rectangle is provided for a better visualization of the collimators solid area and the aperture holes and they are not a part of the structure. Same is for FIG. 14B. Each of the collimators have an aperture made of a circular hole concentric with the collimator rim and two sectors holes, each sector has an angular span of 90 degrees and the sectors are 180 degrees apart. When collimators 1400 and 1402 are placed one on top of the other and concentric, the combined collimator of FIG. 14B is provided. The aperture size and shape of the collimator in FIG. 14B is the same as the size and shape of the aperture of the collimator of FIG. 13A. In the case of the assembly of FIG. 14B however, the angular span of aperture sectors 1404 and 1406 can be modified by rerating collimators 1400 and 1402 relative to each other. This can be done using any of the methods described above in reference to FIG. 11 and FIG. 12.

It would be appreciated that similar designs can provide for variable angular span of the aperture sectors of collimator 1310 of FIG. 13B and other aperture designs.

In the aperture design above, the aperture shape was designed to provide, at a constant rotation speed two areas with two different DPP.

Figure 15A:
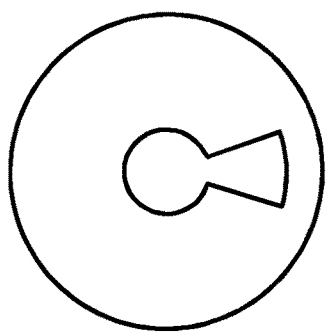
FIG. 15 is a schematic illustration of another 4 example of another collimator of the invention and a qualitative exposure generated by the collimator as a distance from the center of rotation.
Figure 15A:
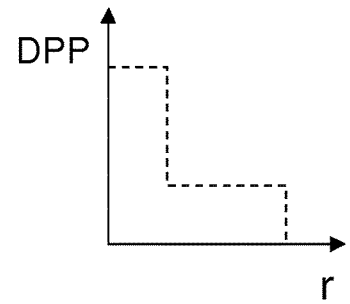
Figure 15B:
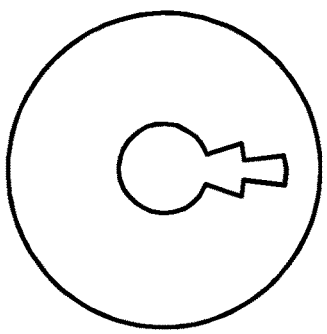
Figure 15B:
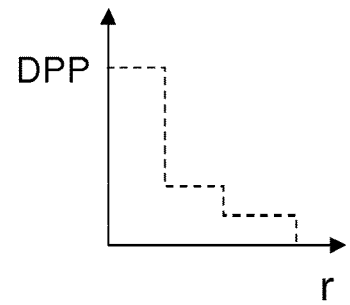
Figure 15C:
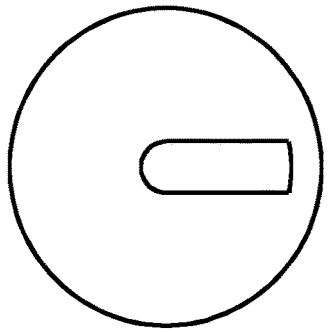
Figure 15C:
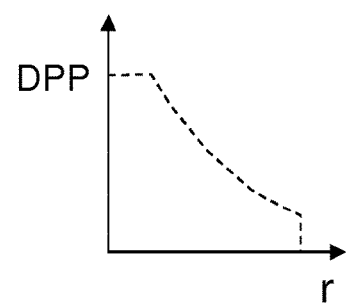
Figure 15D:
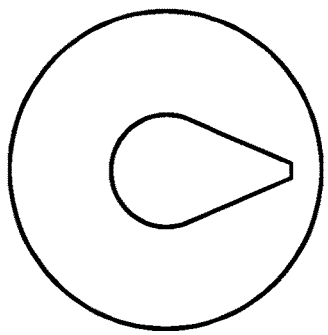
Figure 15D:
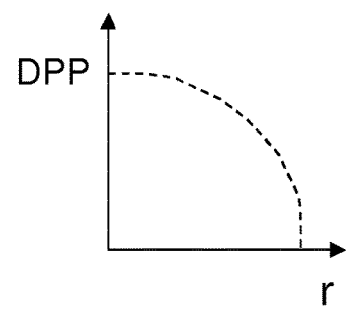

FIG. 15A represents such a collimator and also a qualitative exposure profile showing two levels of DPP for different distances from the center-r. Other apertures can be designed to provide any desired exposure profiles. Some examples are shown in FIG. 15B, FIG. 15C and FIG. 15D. All the collimators of FIG. 15 have aperture design aimed at rotation of 360 degrees for one EC.

Figure 16A:
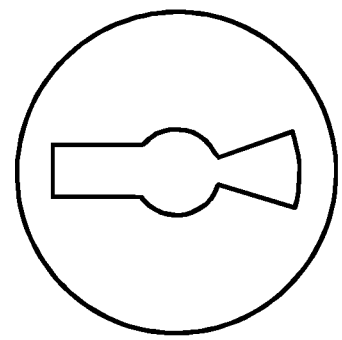
FIG. 16 is a schematic illustration of another 4 example of another collimator of the invention.
Figure 16B:
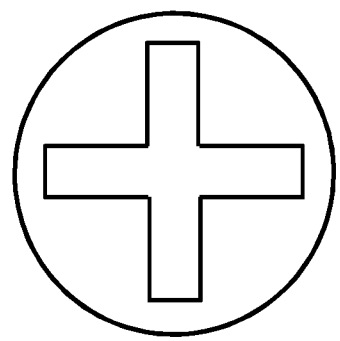
Figure 16C:
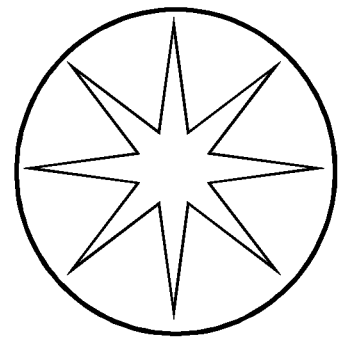
Figure 16D:
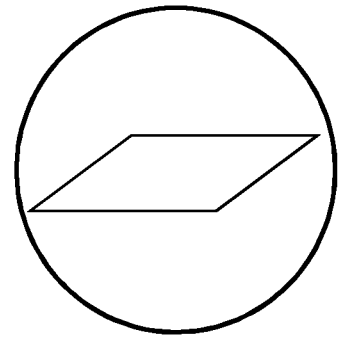

The features of the apertures in the collimators of FIG. 15 can be combined with the features of the apertures in the collimators of FIG. 13. Examples for such combinations are shown in FIG. 16 showing 4 collimators with 4 different aperture designs. In FIG. 16A the left and right halves of the aperture are not symmetrical and one EC requires 360 degrees rotation. FIG. 16B offers a collimator with an aperture providing an exposure profile similar (but not identical) to that of FIG. 15C but one EC consists of 90 degrees rotation only. FIG. 16C offers a collimator with an aperture providing an exposure profile similar (but not identical) to that of FIG. 15D but one EC consists of 360/8=45 degrees rotation only. FIG. 16D offers a collimator with an aperture providing an exposure profile similar (but not identical) to that of FIG. 15D also but one EC consists of 180 degrees rotation only.

Following these examples it is appreciated the invention may be implemented in many designs and it is not limited to a particular design provided hereinabove as an example.

Pixel Correction:

As explained above, pixels with different DPP per the collimator design and use are normalized to provide a proper display-frame. Normalization scheme is made in accordance to the x-ray exposure scheme (i.e., collimator shape, speed and position). Such normalization can be done on the basis of theoretical parameters. For example, in reference to FIG. 7 and FIG. 5, with collimator 500 rotating as a constant speed, the pixels of the annulus incorporating sectors 702 and 704 receive 1/10 the dose of circular area 700 (in this example the angular span 508 of sector 506 is 36 degrees). For simplicity of this example it is assumed that one frame is read from the sensor every time an EC is completed (i.e., collimator 500 completes a rotation of 360 degrees). It will also be assumed that all sensor pixels are of the same response to the image intensifier output and that the image intensifier has uniform response and the x-ray beam from the x-ray tube is uniform. The only built-in (i.e. system level) source of differences between the pixels is from the collimator and the way it is operated. In this example the normalization based on the system design would be a multiplication of pixels by one or 2 factors that will compensate for the difference in DPP.

In one normalization example the values from the pixels of the annulus incorporating sectors 702 and 704 can be multiplied by 10. In another normalization example the values from the pixels of circular area 700 can be multiplied by 1/10. In yet another normalization example the values from the pixels of the annulus incorporating sectors 702 and 704 can be multiplied by 5 and the values from the pixels of circular area 700 can be multiplied by ½.

It would be appreciated that description, explanations and examples of this invention, multiplication and division are completely equivalent and expressions like "multiplying by 1/10" is completely equivalent to expressions like "divide by 10" and whenever multiplication by a value is mentioned it means also the division by reciprocal value alternative and vise-versa. The same holds for multiplication and division symbols used in equations. For example N·B represents also A·C where C=1/B.

The example above is relatively simple since the normalization scheme incorporates 2 knows areas with two known DPP. The situation can become relatively more complicated with different collimators or collimator motion scheme.

In the following example a change is introduced to the rotation of collimator 500. Instead of constant rotation speed a variable rotation speed is used as presented in the following table for one EC (in the case of collimator 500: 360 degrees):

| Sector # | EC range (degrees) | Angular rotation status |
|---|---|---|
| 1 | 0-150 | Constant speed 1 |
| 2 | 150-180 | Constant positive acceleration |
| 3 | 180-330 | Constant speed 2 |
| 4 | 330-360 | Constant negative acceleration |

This rotation pattern together with the convolution with the image pixels, especially in the acceleration sectors, makes it more difficult to estimate normalization the factors.

In the example of the collimators of FIG. 15C and FIG. 15D, many "pixel rings" (pixels at a certain distance from the center) need a suitable normalization factor. Production tolerances of the system that are not included in the theoretical estimation of the normalization factors might result in errors that will show up as ring patterns in the image displayed on monitor 118.

The following calibration method provides calibration that removes the need for theoretical estimation of the factors and also compensates for production tolerances.

In this example any collimator of the invention can be used and any rotation pattern that is fixed per EC can be used.

The fluoroscopic system is set to include all the fixed element relevant to the imaging process (x-ray tube, the desired x-ray operation mode i.e. voltage and current, possible x-ray filter, collimator, patient bed, image intensifier, camera) but none of the variable parts (the patient, the operator's hands and tools). According to this calibration method, the desired collimator is rotated in the desired pattern. A set of raw frame is acquired (using any of the example methods mentioned above). A raw frame is a frame resulting from an integer number of one or more EC with all the pixels of are 712 (FIG. 7), without any manipulation of the pixels. The number of raw frames acquired should be enough to get a relatively good S/N on an average raw frame that is the average of the acquired raw frames. An average raw frame with S/N that is 10 times higher than that of the raw frame is typically sufficient and this can be achieved by averaging 100 raw frames. It would be appreciated that more or less raw frames can be used, depending on the desired quality of the normalized frame.

One average raw frame is created with x-ray off and another with x-ray on.

For this example we assume that the brightness value for each pixel for display purpose ranges from zero to 255. We also select to display a theoretical noiseless frame in the range 5÷250 (darkest noiseless pixel will be displayed at value 5 and the brightest exposed noiseless pixel will be displayed at value 250. This enables noise that brings the pixel values to the range 0÷4 and 251÷255 contribute its statistics appearance to the displayed-frame).

The correction for each pixel i of raw frames j, $P_{ij}$ (j is a frame number index in this example) is calculated using the values of the pixels of the average raw frame made with x-ray radiation on, $A_i$, and values of the pixels of the average raw frame made with x-ray radiation off, $B_i$, to produce the corrected pixel $D_{ij}$ as follows:

$$D_{ij}=(P_{ij}-B_i)\cdot(245/A_i)+5 \quad \text{(Equation 1)}$$

In yet a somewhat more simple approach the correction might ignore noise visual aspects at the dark and bright level and simply correct to the display range 0÷255 as follows:

$$D_{ij}=(P_{ij}-B_i)\cdot(255/A_i) \quad \text{(Equation 2)}$$

It would be appreciated that the correction suggested above is linear and works best for systems with relatively linear response of the image intensifier and the camera.

For systems with non linear response, more complicated correction schemes may be used such as bi-linear correction. In this example the range of the values of the pixels is divided roughly to 2 ranges. The current of the x-ray can be reduced, for example to ½ its' normal operation mode so that the DPP is reduced to ½. It is appreciated that the reduced current level depends on the nature of the non linearity and optimal bi-linear correction might require other than ½ of the x-ray current. It would also be appreciated that DPP can be reduced also in other ways such aluminum plates placed right after the collimator.

In this example, with ½ the x-ray current, another set of raw frames is acquired. It would be appreciated that the S/N of these raw frames is lower than that of the raw frames of the standard x-ray current for the specific application. This can be compensated by using more raw frames to generate the average raw frame for ½ the x-ray current, for example 200 raw frames. Let $M_i$ represent the values of the pixels of the average raw frame made with ½ x-ray current radiation on The correction example of Equation 2 is implemented in this example as follows:

For $P_{ij}$ with values less or equal 127

$$D_{ij}=(P_{ij}-B_i)\cdot(127/M_i) \quad \text{(Equation 3)}$$

For $P_{ij}$ with values higher than 127

$$D_{ij}=(P_{ij}-B_i)\cdot(255/A_i) \quad \text{(Equation 4)}$$

It would be appreciated that the x-ray current for $M_i$ might be set to a different level (for example ¼ of the standard current for the specific application) and the equations will assume the form:

For $P_{ij}$ with values less or equal 63

$$D_{ij}=(P_{ij}-B_i)\cdot(63/M_i) \quad \text{(Equation 5)}$$

For $P_{ij}$ with values higher than 63

$$D_{ij}=(P_{ij}-B_i)\cdot(255/A_i) \quad \text{(Equation 6)}$$

It would also be appreciated that if the non-linearity of the pixels is similar between the different pixels within the operating range of the system (that is differences in non linear response are relatively small) correction for non linearity, in most cases is not required. If the application does not require linear response and it is only desired to reduce pixels response non uniformity affects on the displayed frame, then one may skip non-linearity correction.

All pixels corrections can be skipped if the noise pattern resulting from this does not disturb the application. The correction can be made at different sophistication levels (linear, bi-linear, tri-linear, polynomial interpolation and so on) or not at all, as suitable for the application.

Variable ROIs and Variable Rotation Speed Profiles:

In the above examples different rotation profiles with different rotation speeds were described. In the following example rotation profiles of variable speed will be described in the context of ROI in the image. In the examples of the collimators above, a central circular area (such as 600 of FIG. 6 and 700 of FIG. 7) was presented as the ROI and therefore receiving more DPP than the annulus of sectors 702 and 704 that receive lower DPP. This is the trivial case and typically the central area of the image is also the ROI, where the more important part of the image is located. The higher DPP results in higher S/N in this area and therefore provides a better image quality in that area (such as better distinguishable details). Normally, during, for example of a catheter insertion procedure, the patient's bed is moved during the process to keep the tip of the catheter in the range of area 700. Yet, sometimes the area of highest interest in the image moves out of area 700. For example, in reference to FIG. 17A, to the area denoted by numerical indicator 1700.

This might be a result of many reasons such as (1) the catheter tip has moved to area 1700 and the patient has not been moved to bring the catheter tip to area 700 (2) the operator is looking at area 1700 for any reason. This new ROI information can be fed as input to the system in many ways including automatic follow-up on the catheter tip or follow-up of the area to which the operator looks using an eye tracker device (such as EyeLink 1000 available from SR Research Ltd., Kanata, Ontario, Canada) to indicate the desired ROI location to be in conjunction to the gazing point of the user or by using a computer mouse to indicate the desired ROI location.

With angular span of aperture sector 702 and at a constant rotation speed of collimator 500, the DPP in the annulus outside area 700 is $1/10$ of the DPP inside circular area 700 and S/N in the annulus outside area 700 is $1/10^{1/2}$ of that of area 700, resulting in a lower image quality. To overcome this and maintain refreshment rate of the displayed frames of 10 fps with collimator 500 EC of $1/10$ of a second as in the basic example of the invention, the rotation profile can be modified so that the collimator rotation speed in sector 1702 (FIG. 17B) that contains area 700 will be reduced to $1/10$ of the uniform speed and the rotation speed at the rest of the EC will be increased to maintain EC of $1/10$ of a second.

This will be explained now in reference to FIG. 17B and with example of actual numbers.

Let us assume that the angular span of sector 1702 that just contains area 1700 is 54 degrees. The first edge of sector 1702 is 1702A and is located at angular position 63 degrees and edge of 1702B and is located at angular position 117 degrees. That is, sector 1700 is centered on angular position 90 degrees.

In this example, when edge 702A of sector 702 approaches angle 63 degrees (the location of 1702A) the rotation speed of collimator 500 is reduced to 1 rps. This rotation speed is maintained until edge 702B of sector 702 reaches the position of edge 1702B (117 degrees). From this point the rotation speed of collimator 500 is increased again. For simplicity it will be assumed that acceleration and deceleration are extremely high and therefore acceleration and deceleration times are definitely legible for this example. Per the explanation above, collimator 500 rotation profile then includes 54+36=90 degrees ($1/4$ of the EC rotation) at a speed of 1 rps. To compensate for this and complete the EC at an average of 10 rps the rotation speed of collimator 500 at the rest $3/4$ of the EC rotation must be increased to X rps, satisfying the following equation:

$$1 \text{ rps}\cdot 1/4 + X \text{ rps}\cdot 3/4 = 10 \text{ rps} \quad \text{(Equation 7)}$$

Therefore:

$$X \text{ rps} = (10 \text{ rps} - 1 \text{ rps}\cdot 1/4)/(3/4) \quad \text{(Equation 8)}$$

That is, during the rest of the 270 degrees rotation of the EC, the rotation speed should be 13 rps.

With this rotation profile sector 1702 is exposed to the same DPP as area 700 and the S/N of area 1700 is also the same as area 700 as desired.

It would be appreciated that in the sector range outside sector 1702, for which the collimator rotation speed is increased to 13 rps, the DPP will be reduced below that of the DPP of constant rotation speed to $1/13$ the DPP of area 700. It would also be appreciated that area 1700 was presented here as an example do demonstrate the design of rotation profile according to different ROI geometries. Area 1700 might be different in shape and location and it might be possible that more than one ROI is added to the basic ROI of circle 700. Such variations are handled with profile variations of the same concept described above.

It would also be appreciated that acceleration and deceleration mentioned above might take unreliable part of the EC and must be accounted for. Let us assume in the next example that acceleration and deceleration occupy 45 degrees of rotation each and that they are uniform. In this case acceleration has to start 45 degrees before edge 702A arrives at the position of edge 1702A and deceleration starts when edge 702B arrives at the position of 1702B. All other parameters of the system are the same. If X indicates the rotation speed during the 180 degrees of EC and Y is the average rotation speed during each of the 45 degrees acceleration deceleration sectors then the following equation needs to be satisfied to maintain EC of 0.1 s (or average rotation speed of 10 rps):

$$1 \text{ rps}\cdot 1/4 + 2\cdot Y \text{ rps}\cdot 1/8 + X \text{ rps}\cdot 1/2 = 10 \text{ rps} \quad \text{(Equation 9)}$$

Given constant acceleration and deceleration between 1 rps and 10 rps, Y=(1+10)/2=5.5 and the high rotation during 180 degrees is 16.75 rps.

It would be appreciated that this approach presented through the example above is applicable also to other acceleration profiles, other collimators and other operation schemes (such as different fps rates). It would also be appreciated that pixel correction methods described above are fully applicable also to variable rotation speed profiles, Different Refreshment Rates for Different Areas of the Image:

It has been presented above (with the example of collimator 500 of FIG. 5 and operation mode of constant rotation speed of the collimator at 10 rps and display-frame refreshment rate of 10 fps) that the DPP of circular area 700 of FIG. 7 is 10 times higher than the DPP of the annular area constructed of sectors 702 and 704 (to be denoted "annulus" for short). Therefore the S/N in area 700 is also $10^{1/2}$ better than the S/N in the annulus area. The refreshment rate of the entire image 120 (FIG. 2) is the same: 10 fps. The temporal resolution of the entire frame is 0.1 second (s). In the previous example, each display-frame was constructed from the data of one frame acquired from camera 116. Area 200 on the display 118 is equivalent to area 700 on the sensor. Area 200 is exposed to 10 times the DPP of area 202 and the S/N in area 200 is $10^{1/2}$ better than the S/N the annulus area 202. With each EC of collimator 500 the data is read from sensor 714, processed and displayed on monitor 118. The complete image 120 is refreshed then every 0.1 s.

In the following example of the invention it is desired to improve the S/N of annulus 202.

In a first example, while area 200 is refreshed every 0.1 s with the data read from sensor 714, annulus 202 is refreshed only every 1 s. During this 1 s, the data received from sensor 714 for pixels of annulus 202 is used to generate an annulus image that is the sum of the 10 previous frames. In a simplified form, all 10 frames indexed j=1 to 10 are stored. Then for each pixels i in the range of annulus 202 the sum of values is calculated: Pni=Σpij. Pni are then corrected and displayed where n is index number for every set of 10 frames. Therefore for j=1 to 10, the pixels of the sum frames is P1i. For frames j=11 to 20, the pixels of the sum frames is P2i. For frames j=21 to 30, the pixels of the sum frames is P3i and so on. With this example therefore we get a display of image 120 where the S/N of annulus 202 is similar to that of area 200 although annulus 202 receives 1/10 of the DPP in every unit time of area 200. The compromise is that annulus 202 is refreshing every 1 s comparing to every 0.1 s of area 200 and the temporal resolution of annulus 202 is 1 s comparing to 0.1 s of area 200.

In a second example, after the first 10 frames indexed j=1 to 10 were acquired and stored and displayed as the sum of the pixels for annulus 202, refreshment of annulus 202 is made in a different way. Instead of keeping the display of annulus 202 for 1 s until j=11 to 20 are acquired, the displayed image is refreshed after 0.1 s as follows:

Frame j=11 is acquired and stored instead of frame 1. Therefore the previously stored frames 1,2,3,4,5,6,7,8,9,10 the following frames are stored: 11,2,3,4,5,6,7,8,9,10. This set of frames is handled in the same way as the pervious set and annulus 202 is refreshed. After additional 0.1 s frame indexed 12 is acquired and is stored instead of the frame indexed 2: 11,12,3,4,5,6,7,8,9,10. The set is now processed in the same way and annulus 202 display is refreshed. This process repeat itself and as a result annulus area is refreshed every 0.1 s, same as area 200. The temporal resolution of annulus 202 is still 1 s comparing to area 200 with temporal resolution of 0.1 s. The S/N in annulus 202 is similar to the S/N of area 200. In a third example, an intermediate approach is presented. Following the first example, instead of summing pixels of 10 frames and refreshing annulus 202 every 1 s, summing can be done every 5 frames and refreshment od annulus 202 can be made every 0.5 s. The S/N of annulus 202 will be now $\frac{1}{2}^{1/2}$ of the S/N of Area 200 but still better than $\frac{1}{10}^{1/2}$ of the basic example of collimator 500 and the temporal resolution is only 0.5 s comparing to 1 s of the first example of this method.

It would be appreciated that also in the second example an intermediate approach can be used where, instead of replacing each time one of 10 frames, the replacement will be of one frame in a set of 5 frames: 1,2,3,4,5 then 6,2,3,4,5 then 6,6,3,4,5 and so on. Here we gain again the refreshment of annulus 202 every 0.1 s but with temporal resolution of 0.5 s and S/N of annulus 202 will be now $\frac{1}{2}^{1/2}$ of the S/N of Area 200 but still better than $\frac{1}{10}^{1/2}$ of the basic example of collimator 500.

It will be appreciated that this method can be implemented also for collimators that are not rotating collimators such as the one of FIG. 18. FIG. 18A provides a top view of the collimator and FIG. 18B is cross section c-c of FIG. 18A. Collimator 1800 provides a similar function of x-ray reduction as collimators of the invention. It has an aperture 1802 that allows all the radiation in that area pass through, annulus 1806 that reduces the radiation passing through the area at amount depending on the material (typically aluminum) and the thickness of the material and annulus 1804 with thickness changing as a function of the distance from the center, starting at thickness zero on the side of aperture 1802 ending at the thickness of annulus 1806 on the side of annulus 1806. FIG. 18C provides a schematic DPP graph as a function of distance r from the center.

It is assumed that beyond annulus 1806 radiation is fully blocked. For the purpose of the description of this example radiation that is scattered from collimator 1800 is ignored.

For this example it is also assumed that DPP passing through annulus 1806 is 1/10 the DPP passing through aperture 1802. Frame rate is 10 fps and display-frame refreshment rate is 10/s. As described in the above examples S/N of the image part associated with annulus 1806 is $\frac{1}{10}^{1/2}$ of the S/N associated with aperture 1802. To display an image where the S/N of the area associated with annulus 1806 is similar to the S/N in the area associated with aperture 1802 any of the methods above can be used.

Figure 18A:
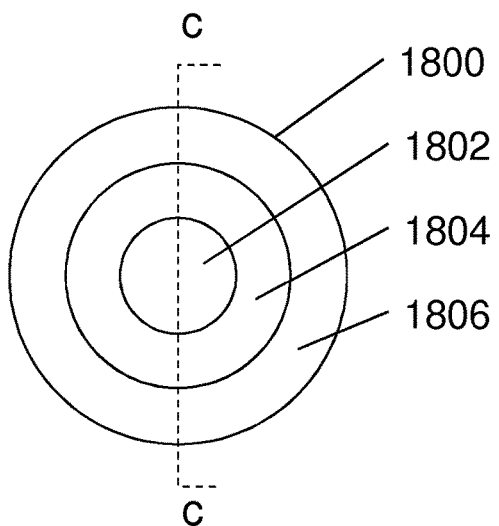
FIG. 18 is a schematic illustration of an example of a non rotating collimator and the effect it has on an image displayed on the monitor.
Figure 18B:
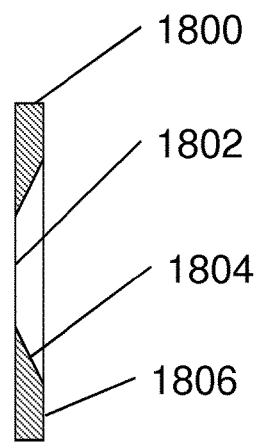
Figure 18C:
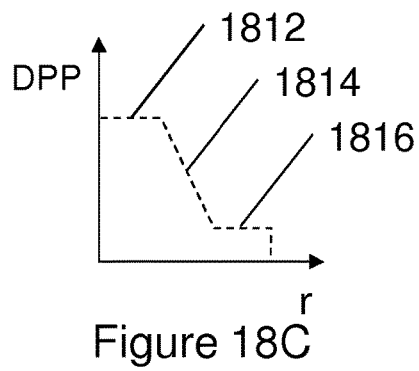
Figure 18D:
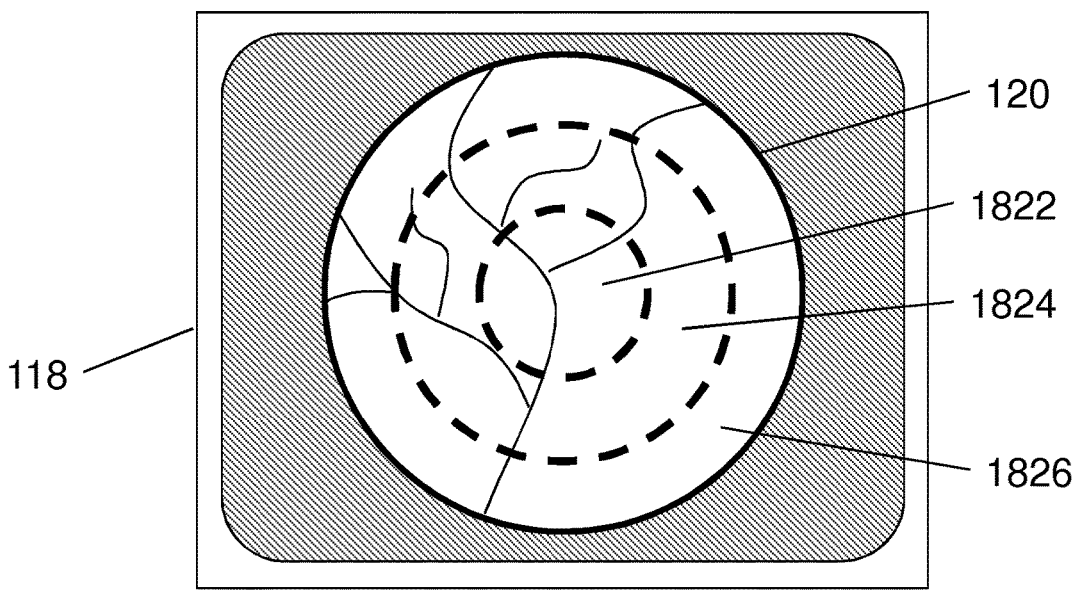

FIG. 18D provides a representation of monitor 118 with the displayed frame associated with collimator 1800. Circle 1822 is the area associated with radiation arriving through aperture 1802 of collimator 1800. Annulus 1824 is the area associated with radiation arriving through annulus 1804 of collimator 1800. Annulus 1826 is the area associated with radiation arriving through annulus 1806 of collimator 1800. It would be appreciated that while the example of annulus 1804 in FIG. 18B is linear change of thickness, the example of change in radiation of 1814 in FIG. 18C is of a non-linear thickness change. That is, many different functions can be used to generate gradient in thickness 1804 to suit the desired gradual change in radiation between annulus 1800 and annulus 1806 of FIG. 18B.

In a first example, while area 1822 is refreshed every 0.1 s with the data read from sensor 714, annulus 1826 is refreshed only every 1 s. During this 1 s, the data received from sensor 714 for pixels of annulus 1826 is used to generate an annulus image that is the sum of the 10 previous frames. In a simplified form, all 10 frames indexed j=1 to 10 are stored. Then for each pixels i in the range of annulus 1826 the sum of values is calculated: Pni=Σpij. Pni are then corrected and displayed where n is index number for every set of 10 frames. Therefore for j=1 to 10, the pixels of the sum frames is P1i. For frames j=11 to 20, the pixels of the sum frames is P2i. For frames j=21 to 30, the pixels of the sum frames is P3i and so on. With this example therefore we get a display of image 120 where the S/N of annulus 1826 is similar to that of area 1822 although annulus 1826 receives 1/10 of the DPP in every unit time of area 1822. The compromise is that annulus 1826 is refreshing every 1 s comparing to every 0.1 s of area 1822 and the temporal resolution of annulus 1826 is 1 s comparing to 0.1 s of area 1822.

For annulus 1824, we shall use here the example where the DPP decreases linearly over the width of annulus 1820 from DPP of 1822 to 1/10 of this DPP, the DPP of annulus 1826.

In this example one may divide annulus 1824 to 8 annuluses of equal radius step so that the average DPP in the smallest annulus #1 is 9/10 of 1822, the average DPP in the next annulus #2 is 8/10 of 1822, annulus #3 is 7/10 and so on until the last annulus #8 that has 2/10 DPP of 1822.

Whenever a value is mentioned in reference to the above segments (annuluses #1 through #8) the value is the average value of that segment in consideration of the thickness variation of the collimator over that segment. When the purpose is to provide on the entire displayed image 120 the same S/N and keep temporal resolution of up to 1 s, it can be done in a simple way for annulus #5 (½ DPP than in area 1822) and annulus #8 (⅕ DPP of area 1822) since the ratio of DPP in area 1822 and the DPP in annulus #5 is an integer. The same is the case for annulus #2.

In the case of annulus #5 adding 2 temporally successive frames as described in any of the above methods (with adequate pixel correction as descried above) will provide S/N similar to area 1822. Temporal resolution in this example will be 0.2 s.

In the case of annulus #8 adding 5 temporally successive frames as described in any of the above methods (with adequate pixel correction as descried above) will provide S/N similar to area 1822. Temporal resolution in this example will be 0.5 s.

For other annuluses (#1, #3, #4, #6, #7 and #8) the ratio of DPP in area 1822 and the DPP in any of these annuluses is not an integer. Therefore adding pixels of an integer number of frames (up to 10 considering the desired limit of not more than 1 s temporal resolution) will exceed the desired S/N or be less than the desired S/N.

To achieve the desired S/N under the requirements of this example following method can be applied:
1. For each annulus #m add the minimum number of pixels of temporally successive frames that provide S/N equal or higher to the S/N of area 1822.
2. Execute pixel correction (offset, normalization and so on as described above).
3. Add noise to each pixel in annulus #m compensate for the cases of S/N higher than in area 1822.

The above steps will be discussed in more details in reference to annulus #1. The DPP in annulus #1 is 9/10 the DPP of area 1822. The S/N in annulus #1 is $(9/10)^{1/2}$ of the S/N in area 1822. Therefore, according to step 1 above we need to add pixels of 2 temporally successive frames in the area of annulus #1 to make the S/N of the pixels in annulus #1 equal or higher than that of area 1822.

By adding the pixels of 2 temporally successive frames in the area of annulus #1 the effective DPP in the resultant frame in annulus 1 is 18/10 of the DPP in area 1822. The S/N in annulus #1 is now $(18/10)^{1/2}$ of the S/N in area 1822. To compensate for the too high S/N (and therefore result in possible visual artifacts in image 120, a Gaussian noise is added to each pixel to satisfy the equation:

$$(N_{1822})^2 = (N_{\#1})^2 + (N_{add})^2 \quad \text{(Equation 10)}$$

Where N1822 is the noise associated with a specific pixel in area 1822 for a specific object transmission, $N_{\#1}$ is the noise associated with the pixel that is the sum of 2 temporally successive pixels pixel in annulus #1 (sum-pixel), having the same object transmission and after the sum-pixel has gone through pixel correction process (including, in the simplest correction form, dividing the value of the summed pixels by 1.8 to bring the affective DPP from 18/10 to 10/10—the same as in area 1822) and $N_{add}$ is the noise to be added to the sum-pixel to bring its' S/N to the same level as the equivalent pixel in area 1822.

In the example above, since the number of x-ray photons in the sum pixel of annulus #1 is 1.8 of the equivalent pixel (same object transmission) of area 1822, the noise of the sum-pixel is $(1.8)^{1/2}$ of the equivalent pixel in area 1822 and the S/N is also $(1.8)^{1/2}$ of the equivalent pixel in area 1822.

To calculate the amount of $N_{add}$ we use equation 10 in the form:

$$N_{add} = ((N_{1822})^2 - (N_{\#1})^2)^{1/2} \quad \text{(Equation 11)}$$

With the pixel correction division by 1.8.
Using Numbers:

$$N_{add} = (1^2 - ((1.8^{1/2})/1.8)^2)^{1/2}$$

$$N_{add} = 0.667$$

Therefore, by adding this poison noise to the sum pixel we provide to that pixel a noise that is similar to the equivalent pixel in area 1822.

It is appreciated that all examples are calculated on a relative basis and therefore the pixel of area 1822 is 1.

It would be appreciated that the noise values in equation 10 are dependent on the pixel value and are typically the square rout of the pixel average level.

The same correction method is applicable to all the segments of annulus 1824 with suitable adjustments.

It would be appreciated that adding pixels of successive frames can be done by adding new frames each time before display-frame refreshment or using the FIFO method as described above.

It would be appreciated that dividing annulus 1824 to 8 segments (Annulus #1 through annulus #8) is provided as an example only. The higher the number of segments, the more uniform the S/N over annulus 1824 will be. Yet, the visibility of the non uniformity of the S/N adjustment is obscured by the S/N of the image therefore, above a certain number of segments the visual contribution of more segments is low and might be undistinguishable to the operator. Therefore one may limit the number of annulus segments in accordance to the S/N statistics of the image in the specific procedure.

The same methods for handling the non-uniform DPP regions such as annulus 1824 of the collimator example 1800 can be used also for collimators of the present invention such as those of FIG. 15C, FIG. 15D and all the collimators of FIG. 16 that also produce non-uniform DPP regions. These methods can be used with any collimator that generates different exposure regions, regardless of the method used by the collimator, whether the different exposure regions are generated by the shape of the collimator, by a motion of the collimator or by combining shape and motion. In all cases of motion of the collimator cycles of the same motion pattern simplify the image enhancement as described above but it is not a requirement to allow the image enhancement described above.

Figure 17A:
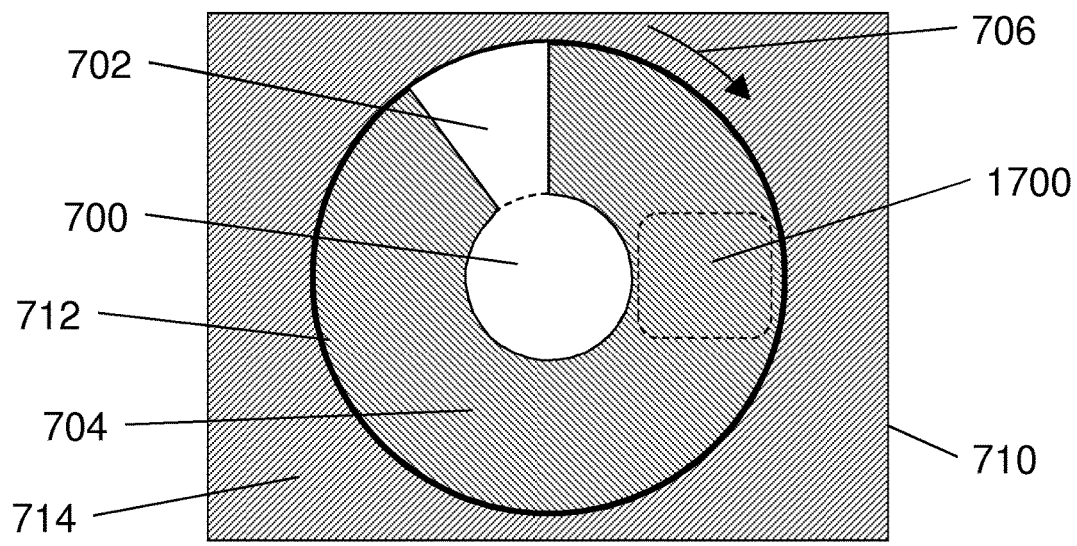
FIG. 17A is a schematic illustration of an example of ROI that is not generally located around the center of rotation.
Figure 17B:
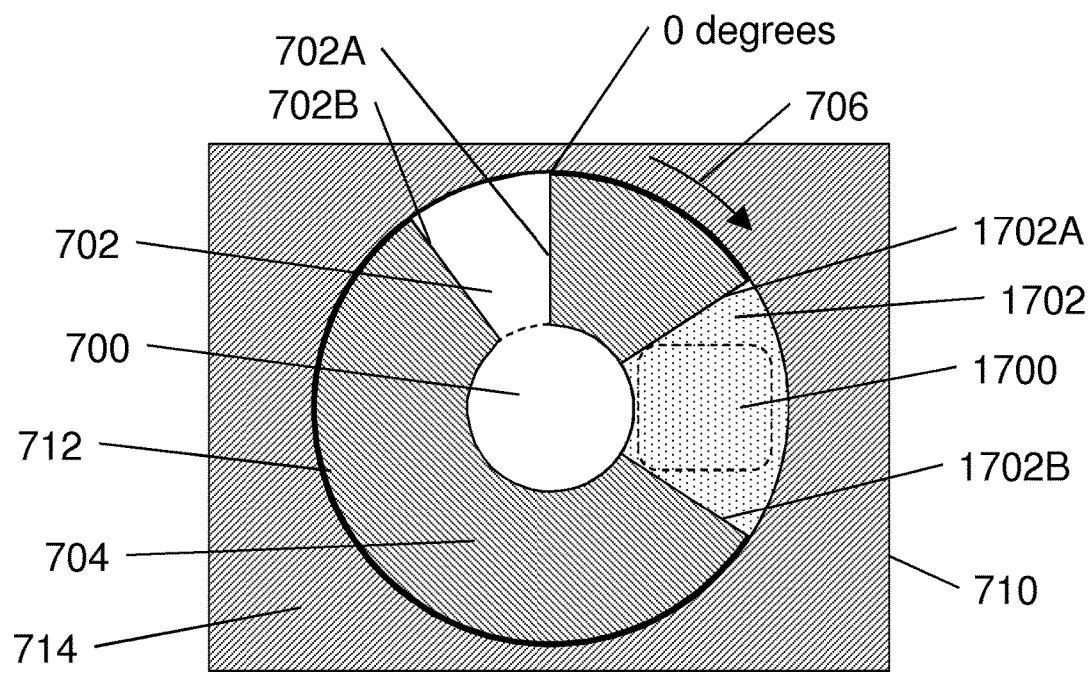
FIG. 17B is a schematic illustration of an example of changing the rotation speed profile of a collimator to enhance the image quality of the ROI of FIG. 17A.
Figure 19A:
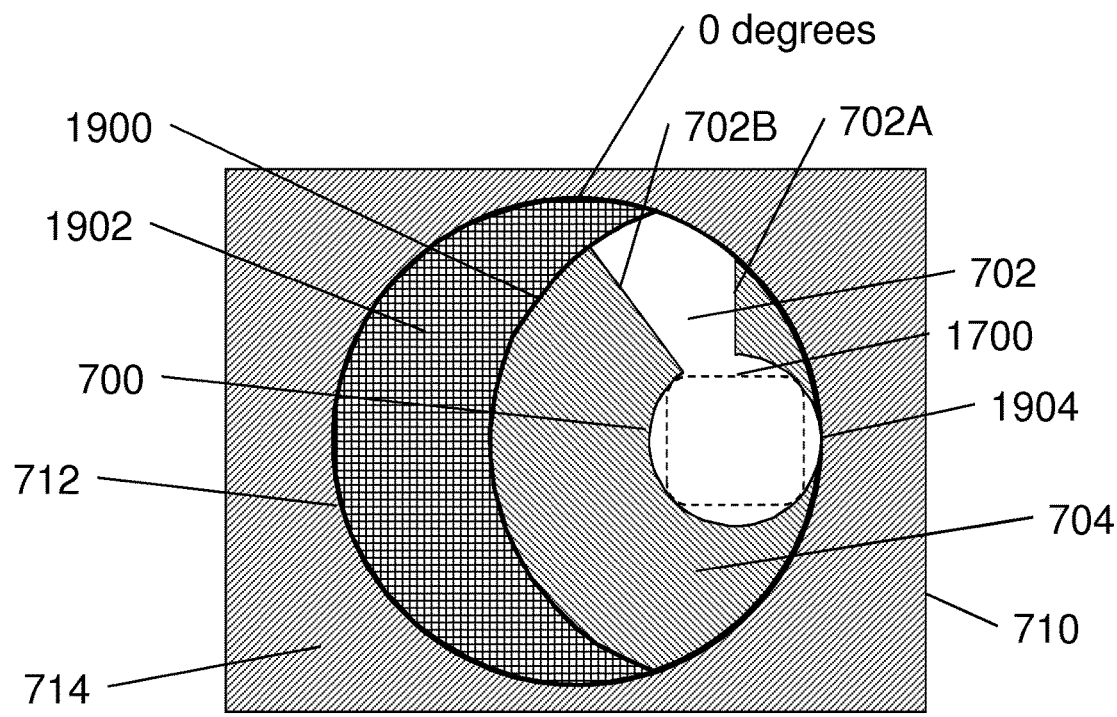
FIG. 19 is an example of the ROI of FIG. 17A and a collimator that can be displaced to bring the center of rotation to generally the center of the ROI.

In yet another example of the invention when the ROI shifts to area 1700 as presented in FIG. 17A, instead of adjusting the rotation profile of collimator 500 as explained in reference to FIG. 17B, the whole collimator can be displaced linearly, in direction parallel to the plane of collimator 500, so that the x-ray radiation passing through circular aperture 504 of FIG. 5 is now centered about area 1700 as shown in FIG. 19A on camera sensor 710.

It is assumed that the only radiation that can arrive at the collimator input surface 112 is radiation that passes through the aperture of collimator 500 (circular hole 505 and sector hole 506). Therefore area 1902 in the sensor is shadowed out in FIG. 19A (no radiation arrives at the corresponding area of image intensifier input 112) and only the area including 700, 702 and 704 limited by boundary 712 is exposed. The exposed area is then the overlap between two circles with centers shifted one relative to the other and indicated in FIG. 19A by the numerical indicator 1900.

This desired function of the invention is provided here within area 1900 by circular hole 504 that enables higher DPP in area 700 and sector hole 506 associated with the rest of the image area enabling only 1/10 of the DPP of hole 504.

Figure 19B:
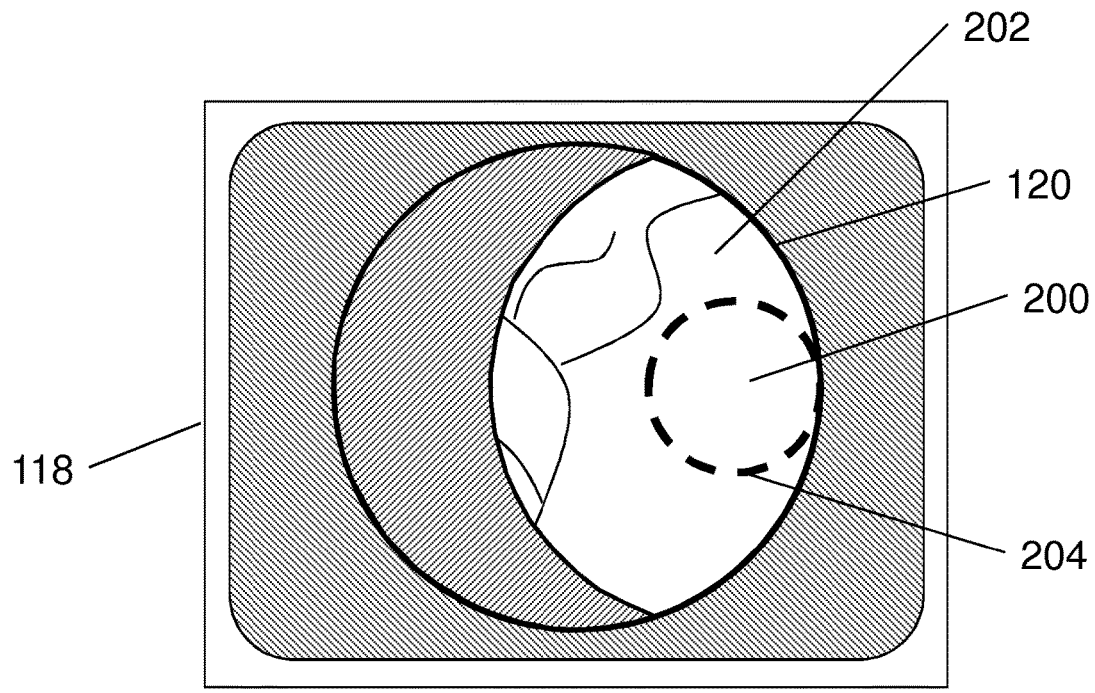

FIG. 19B illustrates the appearance version of FIG. 2 according to the example of FIG. 19A.

Collimator 500 can be moved in X-Y plane (see coordinate system 126 of FIG. 1) using any common X-Y mechanical system. For example, annulus shaped static part 1016 of FIG. 10C is connected to an X-Y system instead of being connected to the x-ray tube structure and the X-Y system is connected to the structure of the X-Y tube, thus enabling the collimator of FIG. 10C, in this example, to move in X-Y plane as desired for the example of FIG. 19A.

It would be appreciated that the above methods such as pixel correction, S/N adjustments, adding pixels of different frames are fully applicable to the example of FIG. 19A with the adjustment of to the displacement of the collimators. The X-Y shift method is applicable to any of the collimators of this invention.

It would be appreciated that also displacement along a line (X axis for example) instead of X-Y can be applied in the same way with the limitation of ROI areas that can be handled this way over image 120 area.

X-Y mechanical systems can assume many designs, including such as Motorized XY Table ZXW050HA02 available from Shanghai ZhengXin Ltd, Shanghai, China. The custom design of X-Y mechanical systems is common in the art and is often made to optimally suit the needs of the application. One such provider of custom designed X-Y mechanical systems is LinTech, Monrovia, Calif., USA.

Figure 20A:
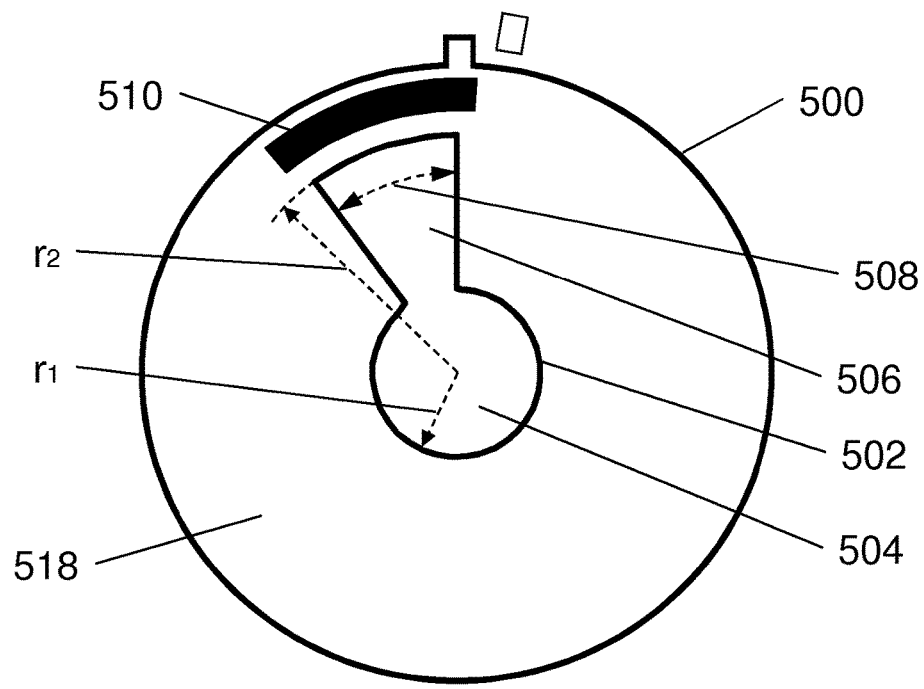
FIG. 20A is the same collimator example of FIG. 5 provided here for visual comparison with the collimator of FIG. 20B.
Figure 20B:
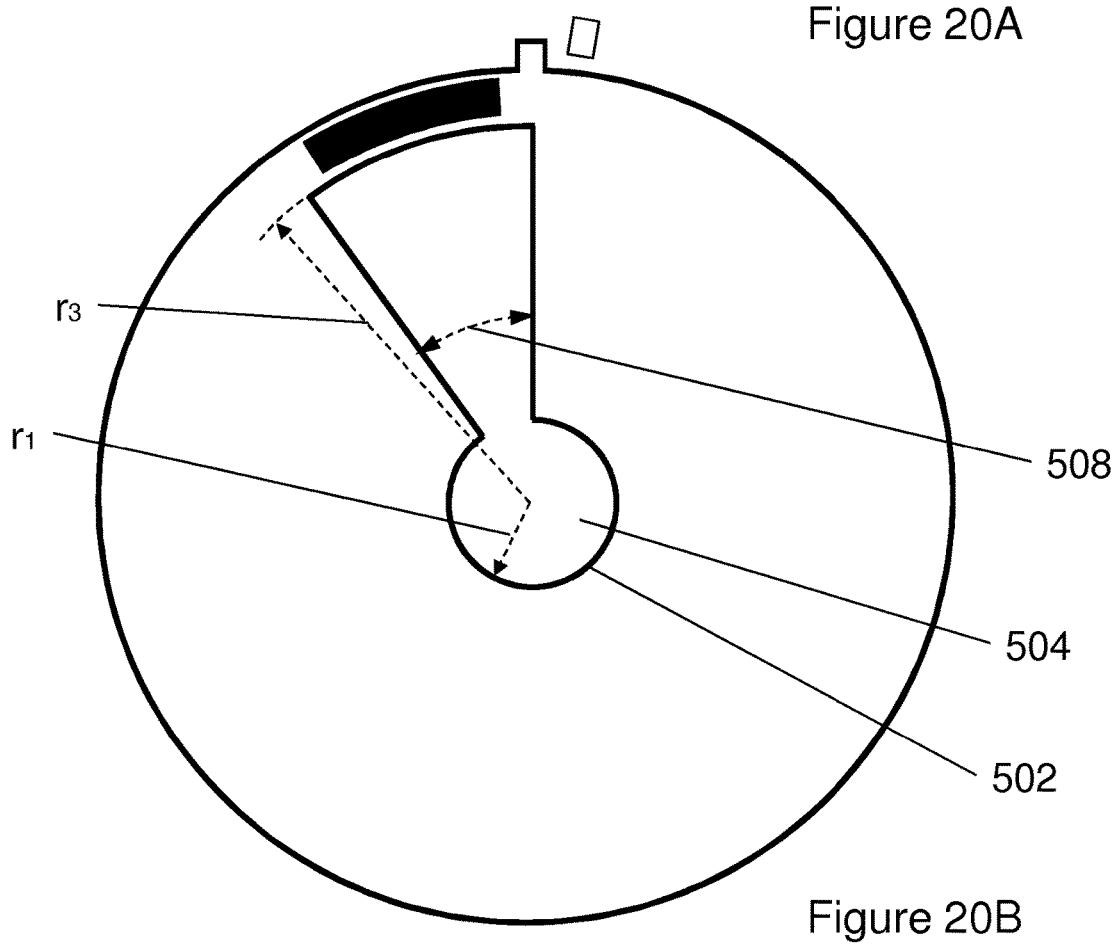
FIG. 20B is an example of a version of the collimator of FIG. 5 with larger diameter and longer sector hole, used to avoid image shadowing during displacement of the collimator.

It would be appreciated that the diameter of collimator 500 can be increased so that the length of sector 702 is increased to r3 as shown in FIG. 20B. FIG. 20A is the collimator of FIG. 5 provided here as FIG. 20A for easy comparison with the collimator of FIG. 20B. Angle 508 is the same (36 degrees in this example), the diameter of circular hole 504 is the same (r1). R3 is large enough to incorporate the complete field of view of image intensifier input 112 also when the collimator is displaced laterally as explained in reference to FIG. 19. With this design, the complete image area 120 of FIG. 19B remains active without any shadowed area such as 1902 in the example of FIG. 19. This collimator enlargement can be implemented in any collimator of the invention.

For the example of FIG. 19, where the maximum displacement desired is up to the point that the edge circular hole 700 is just in one point contact anywhere on the edge of image 712 edge (such one example point is point 1904 in FIG. b19A) the required radius r3 of the sector hole can be calculated as follows, in reference to FIG. 20B:

$$r3 = A - r1 \quad \text{(Equation 12)}$$

Where A is the diameter of the image intensifier input 112B (see FIG. 3) scaled to its' projection in the collimator plane. That is:

$$A = B \cdot (D1/D2) \quad \text{(Equation 13)}$$

In the process of moving the collimator in X-Y plane, pixels that have been exposed to full DPP (through area 504) may change status to be exposed at 1/10 DPP since area 504 has moved and such pixels are not included in that area anymore. It would be appreciated that 1 s a pixel has changes status from being included in area 504 and full DPP to be outside area 504 and 1/10 DPP, considering the operation mode of this example, 10 frames of 1/10 DPP have been already acquired and the processing of this pixel for display is made in any of the methods described above that use last 10 frames to provide S/N same as within area 504 (or 5 frames after 0.5 s in another example). During the 1 s transition another handling is required to keep the S/N of this pixel the same as it was when it was included in area 504.

In this example, with refreshment rate of 0.1 s and temporal resolution that varies from 0.1 s to 1 s the following procedure is implemented, where N is the index of the last full DPP frame for that pixel:

1. At time 0 display for the pixel 100% the last full DPP data of frame N. Temporal resolution is 0.1 s.
2. At time 0.1 s display for the pixel a weighted sum of 90% the last full DPP data of frame N and 100% of the new DPP data of frame N+1.
3. At time 0.2 s display for the pixel a weighted sum of 80% of the last full DPP data of frame N, 100% of the DPP data of frame N+1 and 100% of the DPP data of frame N+2.
4. . . . .
5. . . . .
6. . . . .
7. . . . .
8. . . . .
9. . . . .
10. At time 0.9 s display for the pixel a weighted sum of 10% the last full DPP data of frame N and 100% of the new DPP data of each of frames N+1, N+2, . . . , N+9.
11. At time 1.0 s display for the pixel a weighted sum of 0% the last full DPP data of frame N and 100% of the new DPP data of each of frames N+1, N+2, . . . , N+9, N+10. Temporal resolution has now changed to 1 s.
12. Continue with methods described above for image improvement for 1/10 DPP regions. Temporal resolution will be 1 s.

It would be appreciated that in the case of the method of refreshing the pixels of 1/10 DPP in a rate of only 1 fps the last full DPP data will be presented for 1 s after the change of the pixel to 1/10 DPP exposure and afterwards the average of the last 10 frames of 1/10 DPP will be used to refresh the pixel.

In the case that a pixel changes status in the opposite direction, that is changing from 1/10 DPP area to full DPP area, this transition is instant and in the first 0.1 s after the status change the displayed image is refreshed with the first 0.1 s frame of the full DPP.

It would be appreciated as explained in reference to FIG. 1, that the above methods are applicable also for relatively high frequency pulse x-ray. The term "relatively high frequency" is relative to the collimator design and operation mode. In the example of collimator 500 of FIG. 5, that has a sector angular span of 36 degrees and rotates at 10 rps, the pulse frequency should be at least at a frequency of 100/s so that there is at least one x-ray pulse per each 36 degrees area of a frame. To simplify pixel correction scheme, it is also desired that the x-ray pulse frequency would be a positive integer multiplication of minimum frequency. In this example: 200/s, 300/s, 400/s and so on. In this example 1,000/s (10 times the minimum frequency can be considered relatively high frequency.

It is appreciated that no collimator is totally opaque to x-ray and collimators are constructed to block most of the x-ray in the opaque regions. With HVL (half value layer) of 0.25 mm (similar to that of lead), 3 mm thick collimator will allow $0.5^{(3/0.25)} = 1/4096$ of the incident x-ray radiation to pass through (without scatter). The term "essentially opaque" will be used to describe these practical collimators. Most of the collimators described hereinabove are constructed of essentially opaque region such as 518 of FIG. 5 and apertures or holes as 504 and 506 of FIG. 5. Collimators such as the example of FIG. 18 are different since, in addition to the essentially opaque region 1806 and the aperture 1802 they include semi-opaque regions such as 1804 of FIG. 18A.

Collimators according to this invention can be mounted on an x-ray system as stand-alone or together with another collimator, for example, such that is designed to limit the x-ray to a part of input area 112 of the image intensifier. Collimators of the invention and other collimators may be placed in any order along the x-ray path. The exposed part of area 112 will be the remaining of the superposition of the area all the collimators in the path of the x-ray block. In the design of such successive arrangement, the distances of each of the collimators from the x-ray source and distance to area 112 needs to be considered with the geometry of the collimators, as described above, to get the desired functionality.

It would be appreciated by those skilled in the art that the above described methods and technologies are not limited to the configurations and methods mentioned herein above as examples. These are provided as examples and other configurations and methods can be used to optimize final result, depending on the specific design and the set of technologies implemented in the production of the design.

The herein above embodiments are described in a way of example only and do not specify a limited scope of the invention.

The scope of the invention is defined solely by the claims provided herein below:

The invention claimed is:

1. A method of enhancing a displayed exposure image in an x-ray system comprising an x-ray source, a single essentially round collimator, a detector, a monitor and means for moving said collimator in a plane generally parallel to the plane of said collimator, said collimator comprising an aperture that allows all the radiation to pass through, an outer annulus that reduces the radiation passing through at an amount depending on the material and the thickness of the material and an inner annulus between said aperture and said outer annulus, with thickness changing as a function of the distance from the aperture, starting at thickness zero on the side of the aperture and ending at the thickness of the outer annulus on the side of the outer annulus, comprising:

acquiring frames comprising pixels from said detector;

calculating gain and offset for correcting each frame; and calculating normalization factors for correcting each frame, according to the different DPP in each of said aperture, said outer annulus and said inner annulus of the collimator;

wherein calculating normalization factors for said inner annulus comprises dividing said inner annulus into a plurality of annuli and assigning a single theoretical DPP to each said plurality of annuli depending on its distance from said aperture.

2. The method of claim 1, further comprising tracking an operator's gaze, determining thereby a region of interest (ROI) location and moving said collimator accordingly.

* * * * *